United States Patent
Connolly et al.

(10) Patent No.: US 7,384,979 B2
(45) Date of Patent: Jun. 10, 2008

(54) SUBSTITUTED AMINO ACIDS AS ERYTHROPOIETIN MIMETICS

(75) Inventors: Peter J. Connolly, New Providence, NJ (US); William V. Murray, Belle Mead, NJ (US); Steven K. Wetter, Flemington, NJ (US); Sigmond Johnson, Flemington, NJ (US); Victor T. Bandurco, Bridgewater, NJ (US); Jacqueline Bussolari, Skillman, NJ (US)

(73) Assignee: Ortho McNeil Pharmaceutical, Inc., Raritan, NJ (US)

(*) Notice: Subject to any disclaimer, the term of this patent is extended or adjusted under 35 U.S.C. 154(b) by 0 days.

(21) Appl. No.: 11/442,920

(22) Filed: May 30, 2006

(65) Prior Publication Data

US 2006/0247274 A1    Nov. 2, 2006

Related U.S. Application Data

(62) Division of application No. 10/799,324, filed on Mar. 12, 2004, now Pat. No. 7,153,869, which is a division of application No. 09/927,111, filed on Aug. 10, 2001, now Pat. No. 6,750,369, which is a division of application No. 09/517,976, filed on Mar. 3, 2000, now Pat. No. 6,310,078, which is a division of application No. 09/294,785, filed on Apr. 19, 1999, now abandoned.

(60) Provisional application No. 60/082,392, filed on Apr. 20, 1998.

(51) Int. Cl.
*A61K 31/235* (2006.01)
*A61K 31/24* (2006.01)
*A61K 31/195* (2006.01)
*A61K 31/40* (2006.01)

(52) U.S. Cl. .................. 514/533; 514/419; 514/538; 514/542; 514/562; 514/563; 514/564; 514/566

(58) Field of Classification Search ............. None
See application file for complete search history.

(56) References Cited

OTHER PUBLICATIONS

Database CAPLUS on STN, Acc, No. 1997:711911, Coldham et al., Journal of the Chemical Society, Perkin Transactions 1: Organic and Bio-Organic Chemistry (1997), (20), p. 2951-2952 (abstract).*
Database CAPLUS on STN, Acc, No. 1978:510293, Halstrom et al., Journal of Chemical Research, Synopses (1978), (2), p. 80-81 (abstract).*

* cited by examiner

*Primary Examiner*—Brian Davis
(74) *Attorney, Agent, or Firm*—Yunling Ren

(57) ABSTRACT

This invention relates to a series of substitituted amino acids of Formula I

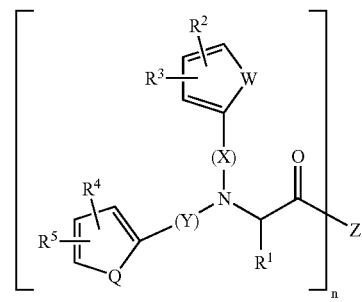

pharmaceutical compositions containing them and intermediates used in their manufacture. The compounds of the invention are small molecules which bind to the erythropoietin receptor and compete with the natural ligand for binding to this receptor.

16 Claims, No Drawings

SUBSTITUTED AMINO ACIDS AS ERYTHROPOIETIN MIMETICS

CROSS REFERENCE TO RELATED APPLICATIONS

This application is a divisional of Ser. No. 10/799,324, now Pat. No. 7,153,869, filed Mar. 12, 2004, which is a divisional of Ser. No. 09/927,111, now Pat. No. 6,750,369, filed Aug. 10, 2001, which is a divisional of Ser. No. 09/517,976, now Pat. No. 6,310,078, filed Mar. 3, 2000, which is a divisional of Ser. No. 09/294,785, now abandoned, filed Apr. 19, 1999, which claims priority from a Provisional Ser. No. 60/082,392, filed Apr. 20, 1998. The complete disclosures of the aforementioned applications are incorporated herein by reference in their entirety.

This invention relates to a series of small molecules which bind to the erythropoietin receptor and compete with the natural ligand for binding to said receptor. The invention includes pharmaceutical compositions containing these mimetics, their methods of production as well as intermediates used in their synthesis.

Erythropoietin (EPO) is a 34,000 dalton glycoprotein hormone which is produced in the mammalian kidney. Its primary role is stimulation of mitotic cell division and differentiation of erythrocyte precursor cells. As a result this hormone regulates the production of erythrocytes, the hemoglobin contained therein and the blood's ability to carry oxygen. The commercial product Epogen® is used in the treatment of anemia. This drug is produced by recombinant techniques and is formulated in aqueous isotonic sodium chloride/sodium citrate. Even though it has been, used successfully in the treatment of anemia, it is a costly drug that is administered intravenously. This method of administration is both costly and inconvenient for the patient; therefore it would be desirable to find a EPO mimetic which has the potential for oral activity.

A small molecule EPO mimetic has advantages over the natural protein. The immune response associated with large peptides is unlikely to occur with small molecules. In addition, the variety of pharmaceutical formulations that may be used with small molecules are technically unfeasible for proteins. Thus the use of relatively inert formulations for small molecules is possible. The most important advantage of small molecules is their potential for oral activity. Such an agent would ease administration, cost less and facilitate patient compliance.

Although compounds which mimic EPO are useful in stimulating red blood cell synthesis, there are diseases where the overproduction of red blood cells is a problem. Erythroleukemia and polysythemia vera are examples of such diseases. Since EPO is an agent responsible for the maturation of red blood cell precursors, an antagonist of EPO would have utility treating either of those diseases.

SUMMARY OF THE INVENTION

The disclosed invention consists of a series of small molecules which demonstrate competitive binding with the natural ligand for the EPO receptor. As such these compounds are potentially useful in the treatment of diseases or conditions associated with this receptor. In addition, the invention contemplates methods of producing these compounds and intermediates used in their production.

The invention includes compounds of the Formula I:

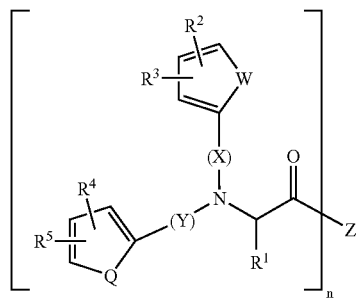

wherein:

$R^1$ is the side chain of a natural or unnatural α-amino acids, where if said side chain contains a protectable group, that group may be protected with a member of the group consisting of succinyl, glutaryl, 3,3-dimethylglutaryl, $C_{1-5}$alkyl, $C_{1-5}$alkoxycarbonyl, acetyl, N-(9-fluorenylmethoxycarbonyl), trifluoroacetyl, omega-carboxy$C_{1-5}$alkylcarbonyl, t-butoxycarbonyl, benzyl, benzyloxycarbonyl, 2-chlorobenzyloxycarbonyl, phenylsulfonyl, ureido, t-butyl, cinnamoyl, trityl, 4-methyltrityl, 1-(4,4-dimethyl-2,6-dioxocyclohexylidene)ethyl, tosyl, 4-methoxy-2,3,6-trimethylbenzenesulfonyl, phenylureido, and substituted phenylureido (where the phenyl substituents are phenoxy, halo, $C_{1-5}$alkoxycarbonyl);

$R^2$ and $R^3$ may be taken together to form a six-membered aromatic ring which is fused to the depicted ring, or are independently selected from the group consisting of hydrogen, $C_{1-5}$ alkyl, $C_{1-5}$ alkoxy, hydroxy, halo, trifluoromethyl, nitro, amino, phenyl, phenoxy, phenyl$C_{1-5}$alkyl, phenyl $C_{1-5}$alkoxy, substituted phenyl (where the substituents are selected from $C_{1-5}$alkyl, $C_{1-5}$ alkoxy, hydroxy, halo, trifluoromethyl, nitro, cyano, and is amino), substituted phenoxy (where the substituents are selected from $C_{1-5}$ alkyl, $C_{1-5}$ alkoxy, hydroxy, halo, trifluoromethyl, nitro, cyano, and amino), substituted phenyl$C_{1-5}$alkyl (where the substituents are selected from $C_{1-5}$ alkyl, $C_{1-5}$ alkoxy, hydroxy, halo, trifluoromethyl, nitro, cyano, and amino), substituted phenyl$C_{1-5}$alkoxy (where the substituents are selected from $C_{1-5}$ alkyl, $C_{1-5}$ alkoxy, hydroxy, halo, trifluoromethyl, nitro, cyano, and amino), and substituted amino (where the substituents are selected from one or more members of the group consisting of $C_{1-5}$alkyl, halosubstituted$C_{1-5}$alkyl, $C_{1-5}$alknyl, $C_{1-5}$alkenyl, phenyl, phenyl$C_{1-5}$alkyl, $C_{1-5}$alkylcarbonyl, halo substituted $C_{1-5}$alkylcarbonyl, carboxy$C_{1-5}$alkyl, $C_{1-5}$alkoxy$C_{1-5}$alkyl, cinnamoyl, naphthylcarbonyl, furylcarbonyl, pyridylcarbonyl, $C_{1-5}$alkylsulfonyl, phenylcarbonyl, phenyl$C_{1-5}$alkyl carbonyl, phenylsulfonyl, phenyl$C_{1-5}$alkylsulfonyl substituted phenylcarbonyl, substituted phenyl$C_{1-5}$alkylcarbonyl, substituted phenylsulfonyl, substituted phenyl$C_{1-5}$alkylsulfonyl, substituted phenyl, and substituted phenyl$C_{1-5}$alkyl [where the aromatic phenyl, phenylC$_{1-5}$alkyl, phenylcarbonyl, phenyl C$_{1-5}$alkylcarbonyl, phenylsulfonyl, and phenylC$_{1-5}$ alkylsulfonyl substitutents are independently selected from one to five members of the group consisting of C$_{1-5}$alkyl, C$_{1-5}$alkoxy, hydroxy, halogen, trifluoromethyl, nitro, cyano, and amino]);

R$^4$ and R$^5$ may be taken together to form a six-membered aromatic ring which is fused to the depicted ring, or are independently selected from the group consisting of hydrogen, C$_{1-5}$ alkyl, C$_{1-5}$ alkoxy, hydroxy, halo, trifluoromethyl, nitro, amino, phenyl, phenoxy, phenylC$_{1-5}$alkyl, phenyl C$_{1-5}$alkoxy, substituted phenyl (where the substituents are selected from C$_{1-5}$alkyl, C$_{1-5}$ alkoxy, hydroxy, halo, trifluoromethyl, nitro, cyano, and amino), substituted phenoxy (where the substituents are selected from C$_{1-5}$ alkyl, C$_{1-5}$ alkoxy, hydroxy, halo, trifluoromethyl, nitro, cyano, and amino), substituted phenylC$_{1-5}$alkyl (where the substituents are selected from C$_{1-5}$ alkyl, C$_{1-5}$ alkoxy, hydroxy, halo, trifluoromethyl, nitro, cyano, and amino), substituted phenylC$_{1-5}$alkoxy (where the substituents are selected from C$_{1-5}$ alkyl, C$_{1-5}$ alkoxy, hydroxy, halo, trifluoromethyl, nitro, cyano, and amino), and substituted amino (where the substituents are selected from one or more members of the group consisting of C$_{1-5}$alkyl, halosubstitutedC$_{1-5}$alkyl, C$_{1-5}$alknyl, C$_{1-5}$alkenyl, phenyl, phenylC$_{1-5}$alkyl, C$_{1-5}$alkylcarbonyl, halo substituted C$_{1-5}$alkylcarbonyl, carboxyC$_{1-5}$alkyl, C$_{1-5}$alkoxyC$_{1-5}$alkyl, cinnamoyl, naphthylcarbonyl, furylcarbonyl, pyridylcarbonyl, C$_{1-5}$alkylsulfonyl, phenylcarbonyl, phenylC$_{1-5}$alkyl carbonyl, phenylsulfonyl, phenylC$_{1-5}$alkylsulfonyl substituted phenylcarbonyl, substituted phenylC$_{1-5}$ alkylcarbonyl, substituted phenylsulfonyl, substituted phenylC$_{1-5}$alkylsulfonyl, substituted phenyl, and substituted phenylC$_{1-5}$alkyl [where the aromatic phenyl, phenylC$_{1-5}$alkyl, phenylcarbonyl, phenyl C$_{1-5}$alkylcarbonyl, phenylsulfonyl, and phenylC$_{1-5}$ alkylsulfonyl substitutents are independently selected from one to five members of the group consisting of C$_{1-5}$alkyl, C$_{1-5}$alkoxy, hydroxy, halogen, trifluoromethyl, nitro, cyano, and amino]);

W is selected from the group consisting of —CH=CH—, —S—, and —CH=N—;

Q is selected from the group consisting of —CH=CH—, —S—, and —CH=N—;

X is selected from the group consisting of carbonyl, C$_{1-5}$alkyl, C$_{1-5}$alkenyl, C$_{1-5}$alkenylcarbonyl, and (CH$_2$)$_m$—C(O)— where m is 2-5;

Y is selected from the group consisting of carbonyl, C$_{1-5}$alkyl, C$_{1-5}$alkenyl, C$_{1-5}$alkenylcarbonyl, and (CH$_2$)$_m$—C(O)— where m is 2-5;

n is 1, 2, or 3;

Z is selected from the group consisting of hydroxy, C$_{1-5}$ alkoxy, phenoxy, phenylC$_{1-5}$alkoxy, amino, C$_{1-5}$alkylamino, diC$_{1-5}$alkylamino, phenylamino, phenylC$_{1-5}$ alkylamino, piperidin-1-yl substituted piperidin-1-yl (where the substituents are selected from the group consisting of C$_{1-5}$alkyl, C$_{1-5}$alkoxy, halo, aminocarbonyl, C$_{1-5}$alkoxycarbonyl, and oxo;

substituted phenylC$_{1-5}$alkylamino (where the aromatic substitutents are selected from the group consisting of C$_{1-5}$alkyl, C$_{1-5}$alkoxy, phenylC$_{1-5}$alkenyloxy, hydroxy, halogen, trifluoromethyl, nitro, cyano, and amino), substituted phenoxy (where the aromatic substitutents are selected from the group consisting of C$_{1-5}$alkyl, C$_{1-5}$alkoxy, hydroxy, halogen, trifluoromethyl, nitro, cyano, and amino), substituted phenylC$_{1-5}$alkoxy (where the aromatic substitutents are selected from the group consisting of C$_{1-5}$alkyl, C$_{1-5}$alkoxy, hydroxy, halogen, trifluoromethyl, nitro, cyano, and amino), —OCH$_2$CH$_2$(OCH$_2$CH$_2$)$_s$OCH$_2$CH$_2$O—, —NHCH$_2$CH$_2$(OCH$_2$CH$_2$)$_s$OCH$_2$CH$_2$NH—, —NH(CH$_2$)$_p$O(CH$_2$)$_q$O(CH$_2$)$_p$NH—, —NH(CH$_2$)$_q$NCH$_3$(CH$_2$)$_s$NH—, —NH(CH$_2$)$_s$NH—, and (NH(CH$_2$)$_s$)$_3$N, where s, p, and q are independently selected from 1-7 with the proviso that if n is 2, Z is not hydroxy, C$_{1-5}$ alkoxy, amino, C$_{1-5}$alkylamino, diC$_{1-5}$alkylamino, phenylamino, phenylC$_{1-5}$alkylamino, or piperidin-1-yl, with the further proviso that if n is 3, Z is (NH(CH$_2$)$_s$)$_3$N.

and the salts thereof.

DETAILED DESCRIPTION OF THE INVENTION

The terms used in describing the invention are commonly used and known to those skilled in the art. "Independently" means that when there are more than one substituent, the substitutents may be different. The term "alkyl" refers to straight, cyclic and branched-chain alkyl groups and "alkoxy" refers O-alkyl where alkyl is as defined supra. "Cbz" refers to benzyloxycarbonyl. "Boc" refers to t-butoxycarbonyl and "Ts" refers to toluenesulfonyl. "DCC" refers to 1,3-dicyclohexylcarbodiimide, "DMAP" refers to 4-N',N-dimethylaminopyridine and "HOBT" refers to 1-hydroxybenzotriazole hydrate. "Fmoc" refers to N-(9-fluorenylmethoxycarbonyl), "DABCO" refers to 1,4-Diazabicyclo[2.2.2]octane, "EDCI" refers to 1-(3-dimethylaminopropyl)-3-ethylcarbodiimide, "Dde" refers to 1-(4,4-dimethyl-2,6-dioxocyclohexylidene)ethyl, and "TMOF" refers to trimethyl orthoformate. The side chains of α-amino acids refer to the substituents of the stereogenic carbon of an α-amino acid. For example if the amino acid is lysine, the side chain is 1-aminobutan-4-yl. The term natural amino acid refers to the 20 α-amino acids of the L configuration which are found in natural proteins. Unnatural α-amino acids include synthetic amino acids such as, α-aminoadipic acid, 4-aminobutanoic acid, 6-aminohexanoic acid, α-aminosuberic acid, 5-aminopentanoic acid, p-aminophenylalanine, α-aminopimelic acid γ-carboxyglutamic acid, p-carboxyphenylalanine, carnitine, citrulline, α,β-diaminopropionic acid, α,γ-diaminobutyric acid, homocitrulline, homoserine, and statine as well as D-configuration amino acids. The term "protectable group" refers to a hydroxy, amino, carboxy, carboxamide, guanidine, amidine or a thiol groups on an amino acid side. Compounds of the invention may be prepared by following general procedures known to those skilled in the art, and those set forth herein.

The compounds of the invention may be prepared by liquid phase organic synthesis techniques or by using amino acids which are bound to a number of known resins. The underlying chemistry, namely, acylation and alkylation reactions, peptide protection and deprotection reactions as well as peptide coupling reactions use similar conditions and reagents. The main distinction between the two methods is in the starting materials. While the starting materials for the liquid phase syntheses are the N-protected amino acids or the lower alkyl ester derivatives of either the N-protected or N-unprotected amino acids, the starting material for the resin syntheses are N-protected amino acids which are bound to resins by their carboxy termini.

General Procedure for the Solid-Phase Synthesis of Symmetrical Nα,Nα-Disubstituted Amino Acids
Scheme 1

An equivalent of an N-Fmoc-protected amino acid which is bound to a resin 1a is suspended in a suitable solvent such as DMF. This solvent is removed and the nitrogen protecting group (Fmoc) is removed by stirring the resin bound amino acid with an organic base, such as piperidine, and an addition portion of the solvent. A solution of about two to three equivalents of an appropriately substituted halide, 1b, and a suitable base such DIEA is added to the resin bound amino acid and this mixture is shaken for 18-36 h. The resulting mixture is washed with several portions of a suitable solvent and is suspended and shaken in an acidic solution, such as 50% TFA/CH$_2$Cl$_2$, over several hours to cleave the acid from the resin and give the N-disubstituted amino acid 1c.

By varying the resin bound amino acid 1a, one may obtain many of the compounds of the invention. The following resin bound amino acids may be used in Scheme I: alanine, N-g-(4-methoxy-2,3,6-trimethylbenzenesulfonyl)arginine, β-(4-methyltrityl)asparagine, aspartic acid (β-t-butyl ester), S-(trityl)cysteine, γ-(4-methyltrityl)glutamine, glutamic acid (β-t-butyl ester), glycine, N-imidazolyl-(trityl)histidine, isoleucine, leucine, N-ε-(2-chlorobenzyloxycarbonyl)lysine, N-ε-(t-butoxycarbonyl)lysine, methionine, phenylalanine, proline, O-(t-butyl)serine, O-(t-butyl)threonine, N-indolyl-(t-butoxycarbonyl)tryptophan. O-(t-butyl)tyrosine, valine, β-alanine, α-aminoadipic acid, 4-aminobutanoic acid, 6-aminohexanoic acid, α-aminosuberic acid, 5-aminopentanoic acid, p-aminophenylalanine, α-aminopimelic acid γ-carboxyglutamic acid, p-carboxyphenylalanine, carnitine, citrulline, α,β-diaminopropionic acid, α,γ-diaminobutyric acid, homocitrulline, homoserine, and statine. In addition, the choice of "W" and "X" can be varied by using known halide derivatives of 1b. For example using benzylchloride, 2-chloromethylthiophene, or 2-chloromethylpyridine gives compounds of the invention where "W" is —CH═CH—, —S—, or —CH═N—, respectively. For variations in "X", the use of 2-chloroethylphenyl, 3-chloro-1-propenylbenzene, or benzeneacetyl chloride as 1b, give compounds where Y is (CH$_2$)$_2$, —CH═CH—CH$_2$—, or —CH$_2$C(O)— respectively. Still further, Scheme 1 may be used to produce combinatorial mixtures of products. Using mixtures of resin bound amino acids, 1a, with only one 1b produces said combinatorial mixtures. Alternatively, using one amino acid 1a with a mixture of 1b as well as mixture of 1a with mixtures of 1b gives a large range of combinatorial mixtures.

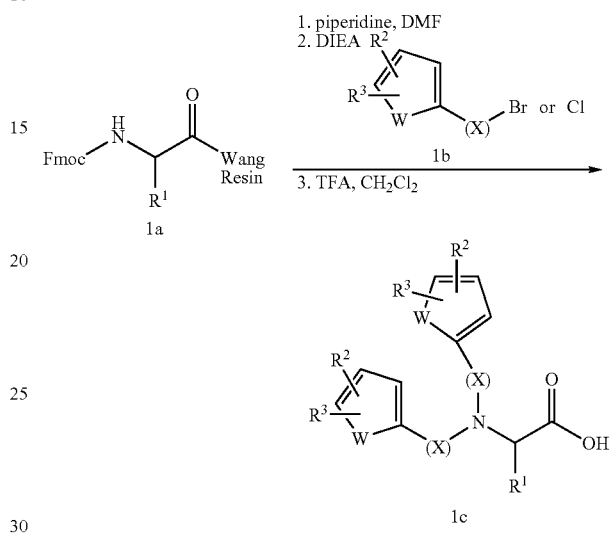

Scheme 1

General Procedure for the Solid-Phase Synthesis of Unsymmetrical Nα,Nα-Disubstituted Amino Acids
Scheme 2, Step A An equivalent of an N-Fmoc-protected amino acid which is bound to a resin 1a is suspended in a suitable solvent such as DMF. This solvent is removed and the nitrogen protecting group (Fmoc) is removed by stirring the resin bound amino acid with an organic base, such as piperidine, and an addition portion of the solvent. Trimethyl orthoformate and an appropriately substituted aldehyde 2a (5 equivalents) is added and the mixture is shaken under N$_2$ overnight. This mixture is treated with a suspension of NaBH(OAc)$_3$ (5 equivalents) in CH$_2$Cl$_2$ and shaken under N$_2$ overnight. After filtration and washing with a suitable solvent, the resulting product, resin bound Nα-monosubstituted amino acid 2b, is rinsed with a suitable solvent and its identity is confirmed by MS and or HPLC analysis after treatmet of a portion of the resin with 50% TFA/CH$_2$Cl$_2$.

Scheme 2, Step B

The resin 2b is suspended in an appropriate solvent such as DMF and is filtered. The appropriately substituted alkyl or arylkyl halide, 2c, and an appropriate base such as DIEA are added with some additional solvent and the mixture is shaken under N$_2$ for 18-36 h. The resin bound Nα,Nα-disubstituted amino acid, 2d, is isolated from the suspension and the resin is cleaved with an acidic solution to give the free acid 2e.

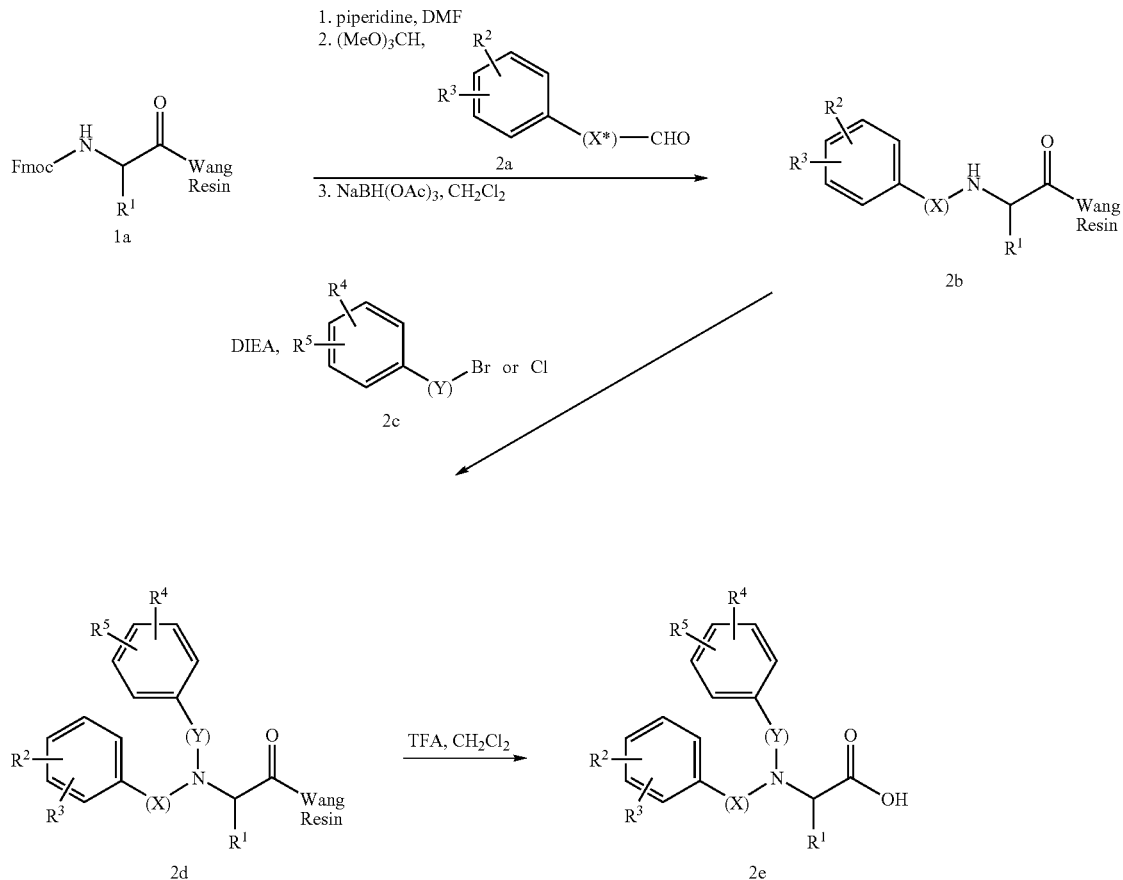

Scheme 3, Step C

A resin bound amine, 2d, where $R^4$ is nitro, is suspended in a suitable solvent, such as DMF, and is filtered. This mixture is treated with $SnCl_2$ dihydrate in DMF and shaken under $N_2$ overnight. The solvent is removed and the resin is washed successive portions of a suitable solvent to give the resin bound compound 3a where $R^4$ is amino. The resin is suspended in a suitable solvent and is combined with an organic base, such as pyridine an appropriately substituted carboxylic acid anhydride, acid chloride, or sulfonyl chloride. The mixture is shaken under $N_2$ overnight and is filtered to give the resin bound amino acid 3b. This material is treated with an acid and a suitable solvent to give the free amino acid 3b.

Scheme 3, Step D

The resin bound amine 3a is treated with TMOF and an appropriately substituted aldehyde 3c is added and the mixture is shaken under $N_2$ overnight. The resulting mixture is drained and treated with a suspension of $NaBH(OAc)_3$ in an appropriate solvent and this mixture is shaken under $N_2$ overnight. The resin bound 3-aralkylaminophenyl amino acid is identified my spectral techniques after clevage to give the free acid 3d as previously described.

Scheme 3, Step E

Resin bound, 2d, where $R^1$ is $(CH_2)_4NH(Dde)$ is mixed with a suitable solvent, such as DMF, and shaken with successive portions of 2% solution of hydrazine hydrate in DMF over about 30 min. The resin is filtered and treated with a suitable solvent and a cyclic anhydride derivative 3e, and a base such as DMAP and pyridine. This mixture is shaken under $N_2$ overnight and filtered to give the resin bound amine, 3f. This material is identified by spectral techniques after cleavage to give the free acid 3f as previously described.

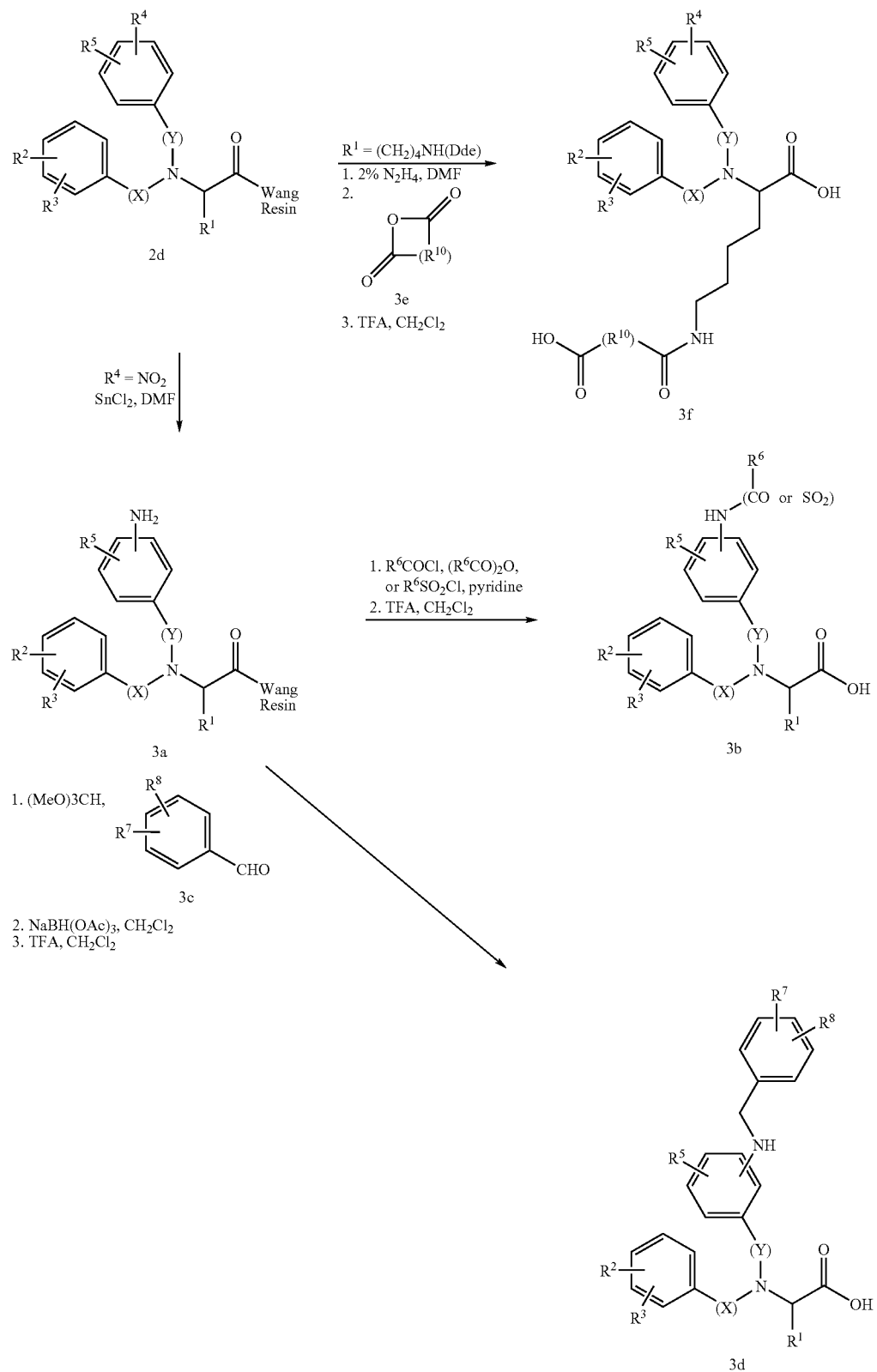

Scheme 4, Step F

Resin bound 2b, where $R^2$ is nitro is suspended in $CH_2Cl_2$ and is treated with an organic base, such as pyridine, and 9-fluorenylmethoxy chloride. This mixture is shaken under $N_2$ overnight, filtered and resuspended in a suitable solvent. This mixture is treated with $SnCl_2$ dihydrate in DMF and shaken under $N_2$ overnight. The solvent is removed and the resin is washed successive portions of a suitable solvent and filtered to give the resin bound compound 4a where $R^2$ is amino. The resin 4a is then suspended in a suitable solvent, such as $CH_2Cl_2$, and is combined with 0.4 mmol of pyridine and 0.25-0.4 mmol of the appropriately substituted carboxylic acid anhydride, acid chloride, or sulfonyl chloride. The mixture is shaken under $N_2$ overnight, filtered, and washed successively with three portions each of $CH_2Cl_2$ and MeOH. This resin is suspended in DMF, filtered, and shaken under $N_2$ with 5 mL of a 40% solution of piperidine in DMF. After 1 h, the solvent is drained and the resin was washed successively with three portions each of suitable solvents to give the resin bound 4b. The identity of the compound was confirmed by spectral analysis after cleveage as previously described.

Scheme 5

The resin 2b (0.2 mmol) is suspended in $CH_2Cl_2$, filtered, and is resuspended in $CH_2Cl_2$. This suspension is treated with diethyl phosphonoacetic acid and diisopropylcarbodiimide or other suitable carbodiimide reagent, and the mixture is shaken under $N_2$ overnight. The solvent is drained and the resulting resin 5a was washed successively with three portions each of $CH_2Cl_2$ and MeOH. The resin is suspended in DMF and filtered. A solution of the appropriately substituted aldehyde 5b (0.6-1.0 mmol) in 3-5 mL of DMF, lithium bromide (0.6-1.0 mmol), and a suitable base such as DIEA or $Et_3N$ (0.6-1.0 mmol) is added and the mixture is shaken under $N_2$ overnight. The solvent is removed and the resin is washed successively with three portions each of DMF, $CH_2Cl_2$, and MeOH. The identity of the resin bound substituted amino acid 5c was confirmed spectral techniques. The resin bound material may be treated with 50% TFA/$CH_2Cl_2$ over 1-1.5 h, to give the acid 5c.

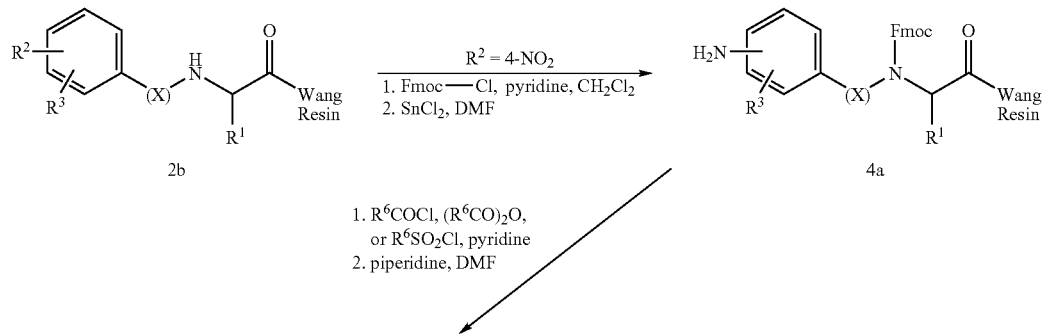

Scheme 4

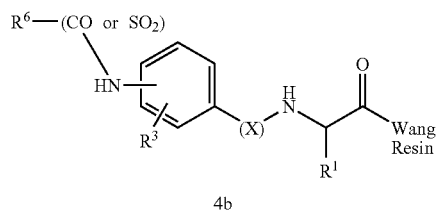

4b

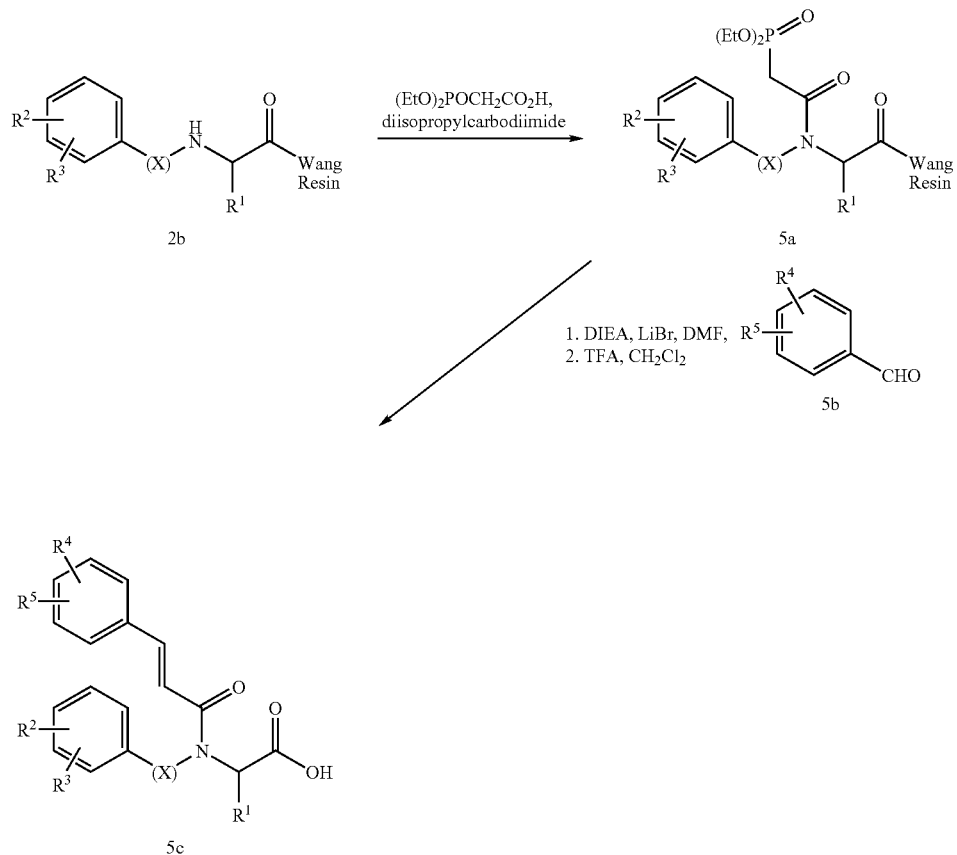
Scheme 6
To prepare compounds where n is 2 and Z is NH(CH$_2$)$_s$NH, products of Schemes 1-5 may be used in Scheme 6. Treatment of two equivalents of the substituted amino acid 1c with an equivalent of the diamine 6a, in the presence of HOBT and a peptide coupling agent such as EDCI and a base such as DIEA at room temperature over 16 h gives the dimer 6b.
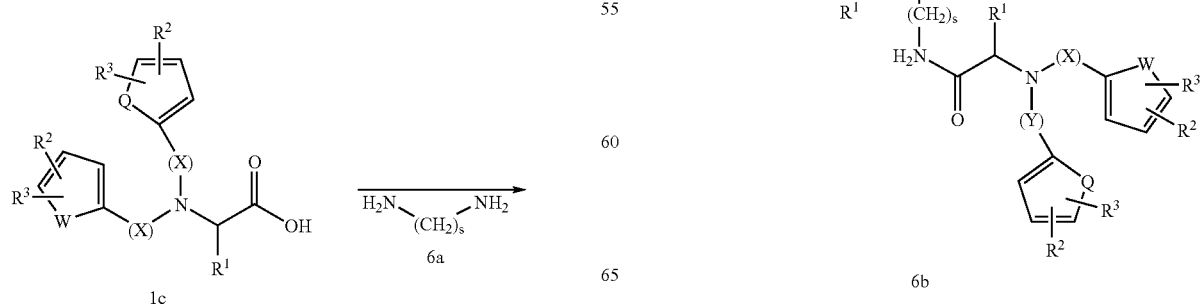

General Procedure for the Solution-Phase Synthesis of Symmetrical Nα,Nα-Disubstituted Amino Acids Scheme 7, Step A A solution of of amino acid ester 7a, an appropriately substituted halide derivitive 1b, and an appropriate base such as DIEA, $Na_2CO_3$, or $Cs_2CO_3$ in a suitable solvent, such as DMF, is heated at 50-100° C. under $N_2$ overnight, or until the starting material is exhausted, to give a mixture of the di and mono-substituted amines, 7b and 7c respectively. If the side chains of $R^1$ contain acid cleavable protecting groups, those groups may be cleaved by treatment with 30-80% $TFA/CH_2Cl_2$. Esters 7b and 7c may be independently converted to the corresponding acids 7d and 7e by hydrolysis with an appropriate base such as aqueous NaOH.

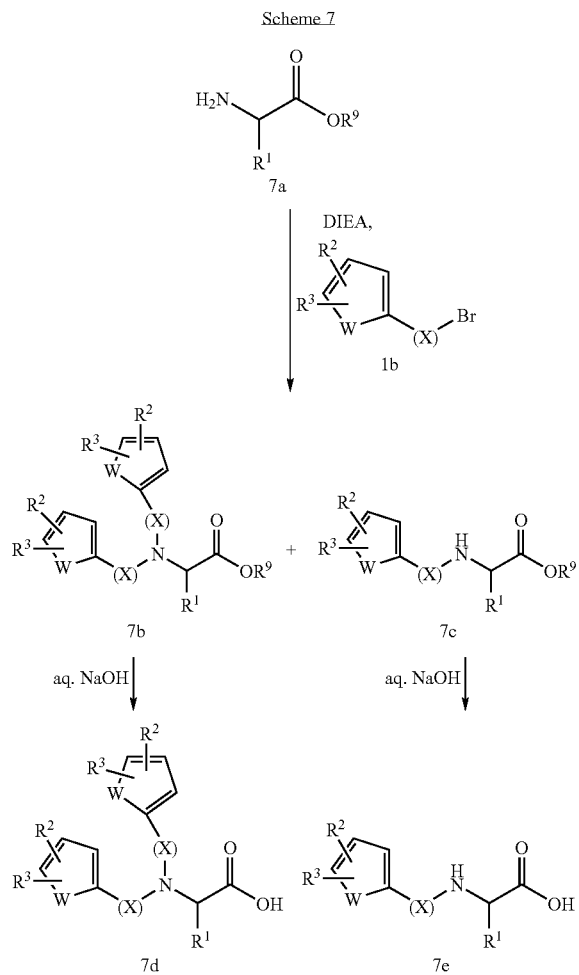

Scheme 7

General Procedure for the Solution-Phase Synthesis of Unsymmetrical Nα,Nα-Disubstituted Amino Acids Scheme 8, Step A A solution of 1 mmol of amino acid ester 8a (or the corresponding HCl salt and 1.1 mmol of DIEA) and 1-1.5 mmol of the appropriately substituted aldehyde 2a in 3-5 mL of trimethyl orthoformate was stirred at room temperature under $N_2$ overnight. The solution was either concentrated and used directly for the next reaction, or was partitioned between EtOAc and water, washed with brine, dried over $Na_2SO_4$, and concentrated to give crude product, which was purified by MPLC to give mono-substituted product 8b.

Scheme 8, Step B

Amino ester 8b was dissolved in DMF, combined with 1.1-1.5 mmol of the appropriately substituted chloride or bromide 2c, and heated at 50-100° C. overnight. The reaction mixture was cooled and partitioned between water and EtOAc. The organic layer was washed three times with water and once with brine, dried over $Na_2SO_4$, and concentrated. The crude product was purified by MPLC to give pure 8c. For examples of 8c wherein the side chain $R^1$ contained an acid-cleavable protecting group such as t-butylcarbamate, t-butyl ester, or t-butyl ether, 8c was stirred in 30-80% $TFA/CH_2Cl_2$ for 1-3 h. The reaction mixture was concentrated and optionally dissolved in HOAc and freeze-dried to give the deprotected form of 8c. For examples of 8c where $R^9$ was equal to t-butyl, 8c was stirred in 30-80% $TFA/CH_2Cl_2$ for 1-3 h and treated as described above to give acid 8d. For examples of 8c where $R^9$ was equal to methyl, ethyl, or other primary or secondary alkyl esters, 8c was stirred with with 1-2 mmol of aqueous LiOH, NaOH, or KOH in MeOH, EtOH, or THF at 20-80° C. until TLC indicated the absence of 8c. The solution was acidified to pH 4-5 with aqueous citric acid or HCl and was extracted with $CH_2Cl_2$ or EtOAc. The organic solution was washed with brine, dried over $Na_2SO_4$, and concentrated to give 8d.

Scheme 8, Step C

For examples of amino acid ester 8c where $R^1=(CH_2)_4$ NHBoc, 8c (1 mmol) was stirred in 30-80% $TFA/CH_2Cl_2$ for 1-3 h. The reaction mixture was concentrated to provide 8e as the TFA salt. Optionally, the TFA salt was dissolved in $CH_2Cl_2$ or EtOAc and washed with aqueous NaOH or $Na_2CO_3$, dried over $Na_2SO_4$, and concentrated to give 8e as the free base.

Scheme 8, Step D

A solution of 1 mmol of 8e, 1-4 mmol of an appropriate base such as DIEA, and 1-2 mmol of the appropriately substituted cyclic anhydride 3e was stirred in $CH_2Cl_2$ or DMF under $N_2$ overnight. The resulting mixture was diluted with $CH_2Cl_2$ or EtOAc and washed with aqueous HCl, water, and brine, was dried over $Na_2SO_4$, and concentrated to provide 8f. Alternatively, 1 mmol of 8e, 1-4 mmol of an appropriate base such as DIEA, and 1-2 mmol of the appropriately substituted carboxylic acid anhydride $(R^{11}CO)_2O$ or acid chloride $R^{11}COCl$ was stirred in $CH_2Cl_2$ or DMF under $N_2$ overnight and worked up as above to provide 8g. Alternatively, 1 mmol of 8e, 1-4 mmol of an appropriate base such as DIEA, and 1-2 mmol of the appropriately substituted isocyanate $R^{12}NCO$ was stirred in $CH_2Cl_2$ or DMF under $N_2$ overnight and worked up as above to provide 8h.

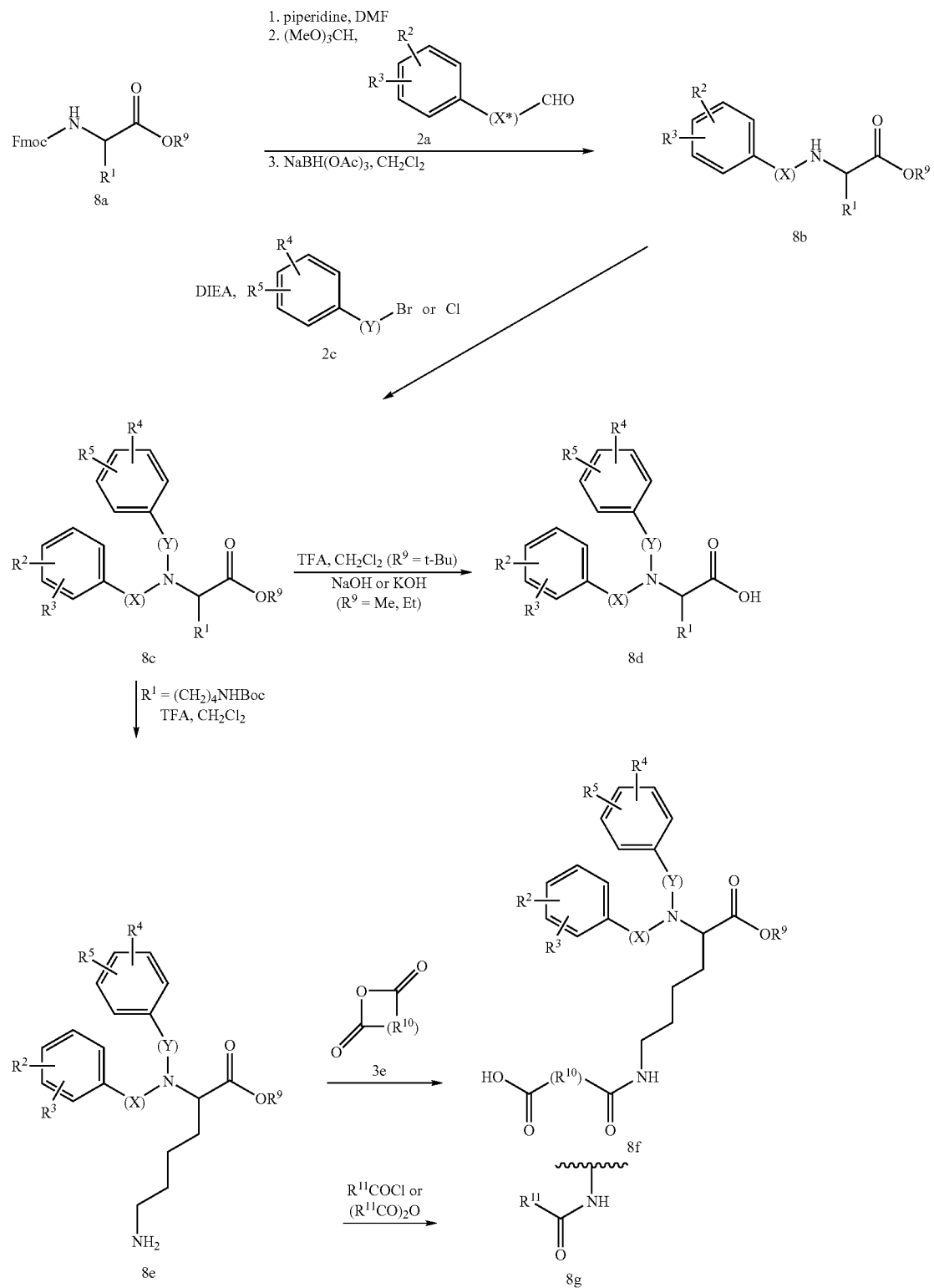

-continued

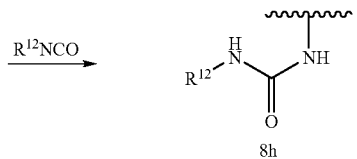

8h

Scheme 9, Step A

For examples of 8c where $R^5=NO_2$, a solution of 1 mmol of 8c (where $R^2$, $R^3$, $R^4$, or) and 10-12 mmol of $SnCl_2$ dihydrate was stirred in MeOH, EtOH, or DMF at 20-80° C. for 0.5-24 h under $N_2$. The solution was taken to room temperature and poured into aqueous $Na_2CO_3$ with rapid stirring. The resulting mixture was extracted with EtOAc or $CH_2Cl_2$ and the organic extracts were washed with brine, dried over $Na_2SO_4$, and concentrated to give the aminophenyl product 9a, which was purified by MPLC or used without further purification.

Scheme 9, Step B

A solution of 1 mmol of aminophenyl compound 9a and 1-1.5 mmol of the appropriately substituted aldehyde 2a in 3-5 mL of trimethyl orthoformate was stirred at room temperature under $N_2$ overnight. The solution was either concentrated and used directly for the next reaction, or was partitioned between EtOAc and water, washed with brine, dried over $Na_2SO_4$, and concentrated to give crude product, which was purified by MPLC to give 9b. For examples of 9b wherein the side chain $R^1$ or $R^9$ contained an acid-cleavable protecting group such as t-butylcarbamate, t-butyl ester, or t-butyl ether, 9b was stirred in 30-80% $TFA/CH_2Cl_2$ for 1-3 h. The reaction mixture was concentrated and optionally dissolved in HOAc and freeze-dried to give the deprotected form of 9b.

Scheme 9, Step C

A solution of 1 mmol of 3-aminophenyl compound 9a, 1.1-2 mmol of pyridine, and 1-1.5 mmol of the appropriately substituted acid chloride, acid anhydride, or sulfonyl chloride in 3-5 mL of $CH_2Cl_2$ or $ClCH_2CH_2Cl$ was stirred at room temperature under $N_2$ overnight. The solution was partitioned between EtOAc and water, washed with water, saturated aqueous $NaHCO_3$, and brine, dried over $Na_2SO_4$, and concentrated to give crude product which was optionally purified by MPLC to give amide or sulfonamide 9c. For examples of 9c wherein the side chain $R^1$ or $R^9$ contained an acid-cleavable protecting group such as t-butylcarbamate, t-butyl ester, or t-butyl ether, 9c was stirred in 30-80% $TFA/CH_2Cl_2$ for 1-3 h. The reaction mixture was concentrated and optionally dissolved in HOAc and freeze-dried to give the deprotected form of 9c.

Scheme 9.

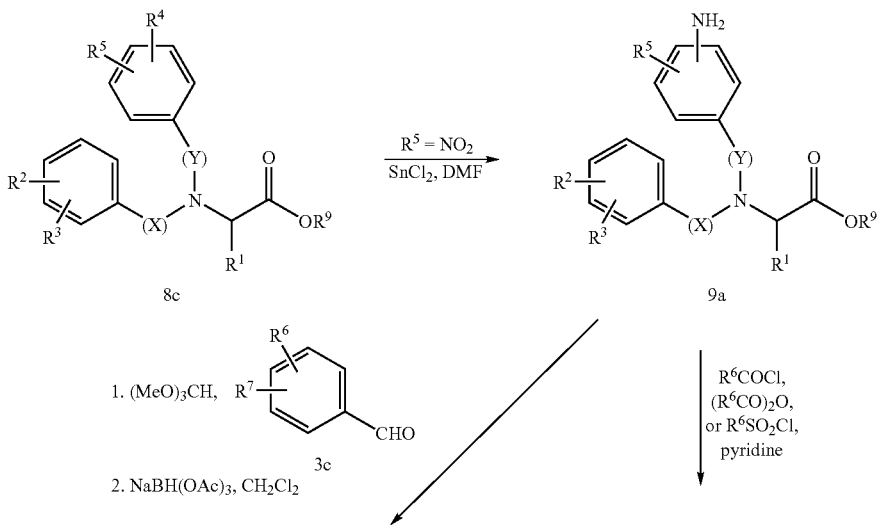

-continued

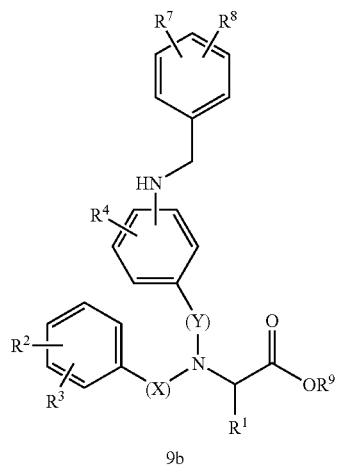

9b

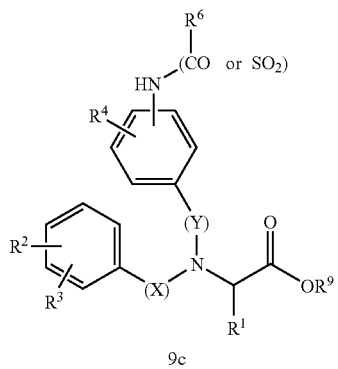

9c

General Procedure for the Solution-Phase Synthesis of Symmetrical Nα,Nα-Disubstituted Amino Amides and their Dimers and Trimers Scheme 10, Step A A solution of 1 mmol of N-Cbz-protected amino acid 10a and the appropriate amine (ZH, 1 mmol), diamine (ZH$_2$, 0.5 mmol), or triamine (ZH$_3$ 0.33 mmol), was treated with 1.1 mmol of HOBt, 1.1 mmol of DIEA, and 2.1 mmol of EDCI in 3-6 mL of CH$_2$Cl$_2$ or DMF. [Alternatively, 1 mmol of the pentafluorophenyl ester or N-hydroxysuccinimide ester of 10a was mixed with the appropriate portion of amine (ZH), diamine (ZH$_2$), or triamine (ZH$_3$) in 3-6 mL of DMF.] The solution was stirred at room temperature under N$_2$ for 12-24 h, and EtOAc was added. The organic solution was washed with 5% aqueous citric acid, water, saturated NaHCO$_3$, and brine, dried over Na$_2$SO$_4$, and concentrated. The crude product was optionally purified by MPLC to afford amide 10b. Compound 10b was stirred in 30-80% TFA/CH$_2$Cl$_2$ for 1-3 h. The reaction mixture was concentrated to provide the TFA salt which was dissolved in CH$_2$Cl$_2$ or EtOAc and washed with aqueous NaOH or Na$_2$CO$_3$, dried over Na$_2$SO$_4$, and concentrated to give 10c as the free base.

Scheme 10, Step B

A solution of 1 mmol of amino acid ester 10c (n=1), 2.5-3 mmol of the appropriately substituted chloride or bromide 2c, and 2.5-3 mmol of an appropriate base such as DIEA, Na$_2$CO$_3$, or Cs$_2$CO$_3$ in 3-5 mL of DMF was heated at 50-100° C. under N$_2$ for 18-24 h. (For examples of 10c where n=2 or 3, the amounts of 2c and base were increased by two- or three-fold, respectively.) The reaction mixture was cooled and partitioned between water and EtOAc. The organic layer was washed three times with water and once with brine, dried over Na$_2$SO$_4$, and concentrated. The crude product was purified by MPLC to give pure amide 10d.

Alternatively, a solution of 1 mmol of amino acid ester 10c (n=1), 2.5-3 mmol of the appropriately substituted aldehyde 2a, and 2.5-3 mmol of borane-pyridine complex in 3-5 mL of DMF or EtOH was stirred at room temperature under N$_2$ for 3-5 days. (For examples of 10c where n=2 or 3, the amounts of 2c and borane-pyridine complex were increased by two- or three-fold, respectively.) The mixture was concentrated to dryness and was partitioned between water and CH$_2$Cl$_2$, washed with brine, dried over Na$_2$SO$_4$, and concentrated. The crude product was purified by MPLC to give pure amide 10d.

Scheme 10, Step C

For examples of 10d where R$^1$=CH$_2$CH$_2$CO$_2$-t-Bu or CH$_2$CO$_2$-t-Bu, 10d was stirred in 30-80% TFA/CH$_2$Cl$_2$ for 1-24 h. The reaction mixture was concentrated and optionally dissolved in HOAc and freeze-dried to give acid 10e.

Scheme 10, Step D

For examples of 10d where R$^1$ is equal to (CH$_2$)$_4$NHBoc, 10d was stirred in 30-80% TFA/CH$_2$Cl$_2$ for 1-24 h. The reaction mixture was concentrated and optionally dissolved in HOAc and freeze-dried to give amine 10f as the TFA salt which was optionally dissolved in CH$_2$Cl$_2$ or EtOAc, washed with aqueous NaOH or Na$_2$CO$_3$, dried over Na$_2$SO$_4$, and concentrated to give 10f as the free base.

Scheme 10, Step E

A solution of 1 mmol of 10f, 1-4 mmol of an appropriate base such as DIEA, and 1-2 mmol of the appropriately substituted cyclic anhydride 3e was stirred in CH$_2$Cl$_2$ or DMF under N$_2$ overnight. The resulting mixture was diluted with CH$_2$Cl$_2$ or EtOAc and washed with aqueous HCl, water, and brine, was dried over Na$_2$SO$_4$, and concentrated to provide acid 10g. Alternatively, 1 mmol of 10f, 1-4 mmol of an appropriate base such as DIEA, and 1-2 mmol of the appropriately substituted carboxylic acid anhydride (R$^{11}$CO)$_2$O or acid chloride R$^{11}$COCl was stirred in CH$_2$Cl$_2$ or DMF under N$_2$ overnight and worked up as above to provide 10 h. Alternatively, 1 mmol of 8e, 1-4 mmol of an appropriate base such as DIEA, and 1-2 mmol of the appropriately substituted isocyanate R$^{12}$NCO was stirred in CH$_2$Cl$_2$ or DMF under N$_2$ overnight and worked up as above to provide 10i.

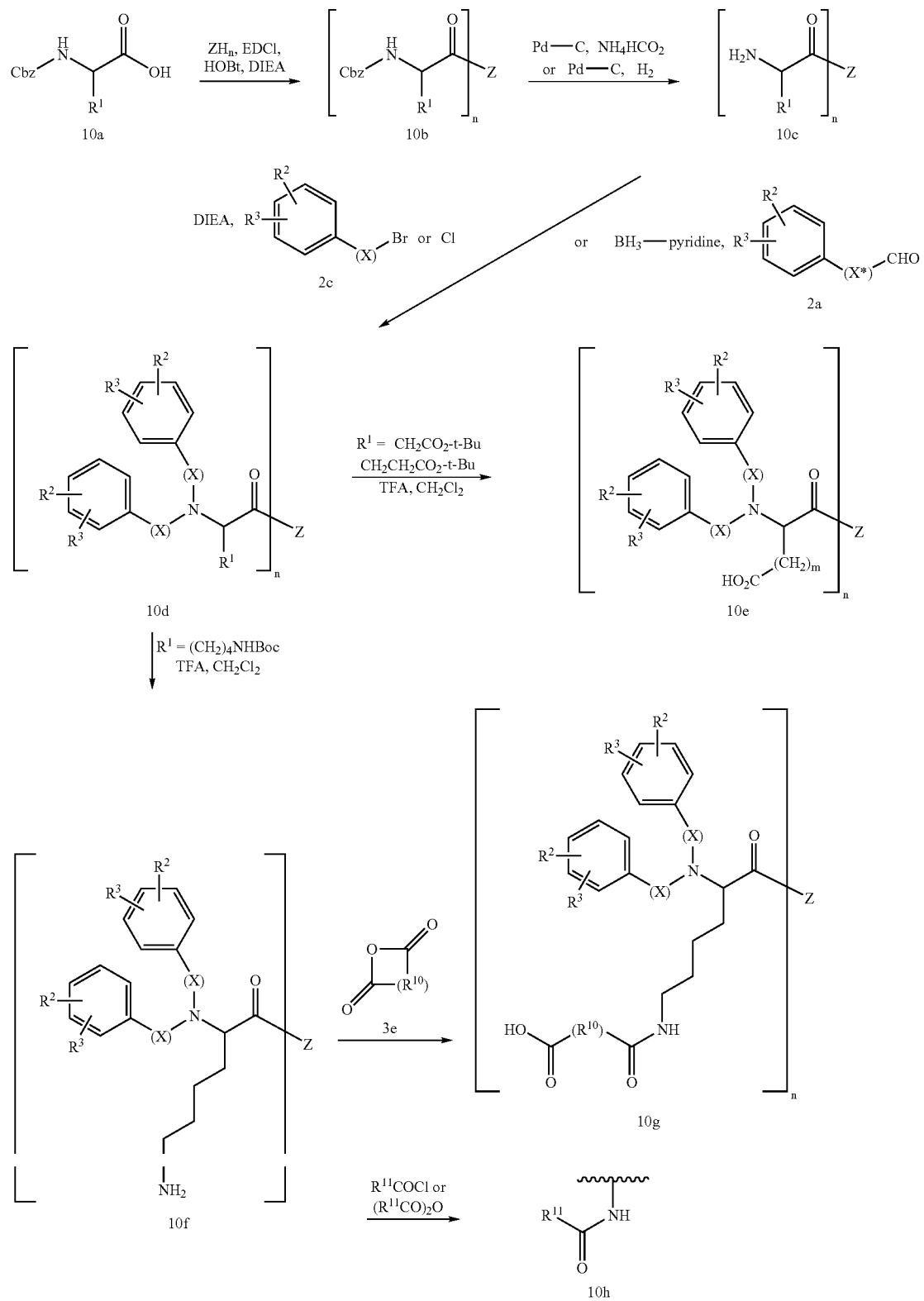

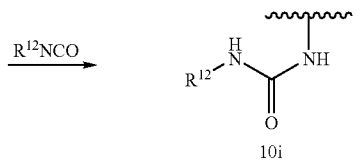

General Procedure for the Solid-Phase Synthesis Of Nα,Nα-Bis-Cinnamyl Amino Acids and Nα-Cinnamyl Amino Acids Scheme 11

An equivalent of an N-Fmoc-protected amino acid 11a which is bound to a polystyrene resin such as Wang resin is suspended in a suitable solvent such as DMF. This solvent is removed and the nitrogen protecting group (Fmoc) is removed by stirring the resin bound amino acid with an organic base, such as piperidine, and an addition portion of the solvent. After filtration and washing with solvent, the resin is suspended in an appropriate solvent such as DMF. A solution of about 2-3 equivalents of an appropriately substituted halide 11b and a suitable base such DIEA is added to the resin bound amino acid and this mixture is shaken for 18-36 h. The resulting mixture is washed with several portions of a suitable solvent and is suspended and shaken in an acidic solution, such as 50% TFA/$CH_2Cl_2$, over several hours to cleave the acid from the resin to give a mixture of the Nα,Nα-bis-cinnamyl amino acid 11c and the Nα-cinnamyl amino acid 11d.

By varying the resin bound amino acid 11a, one may obtain many of the compounds of the invention. The following resin bound amino acids may be used in Scheme 11: alanine, N-g-(4-methoxy-2,3,6-trimethylbenzenesulfonyl) arginine, β-(4-methyltrityl)asparagine, aspartic acid (β-t-butyl ester), S-(trityl)cysteine, γ-(4-methyltrityl)glutamine, glutamic acid (β-t-butyl ester), glycine, N-imidazolyl-(trityl) histidine, isoleucine, leucine. N-ε-(2-chlorobenzyloxycarbonyl)lysine, N-ε-(t-butoxycarbonyl)lysine, methionine, phenylalanine, proline, O-(t-butyl)serine, O-(t-butyl)threonine, N-indolyl-(t-butoxycarbonyl)tryptophan, O-(t-butyl)tyrosine, valine, β-alanine, α-aminoadipic acid, 4-aminobutanoic acid, 6-aminohexanoic acid, α-aminosuberic acid, 5-aminopentanoic acid, p-aminophenylalanine, α-aminopimelic acid γ-carboxyglutamic acid, p-carboxyphenylalanine, carnitine, citrulline, α,β-diaminopropionic acid, α,γ-diaminobutyric acid, homocitrulline, homoserine, and statine.

Scheme 11.

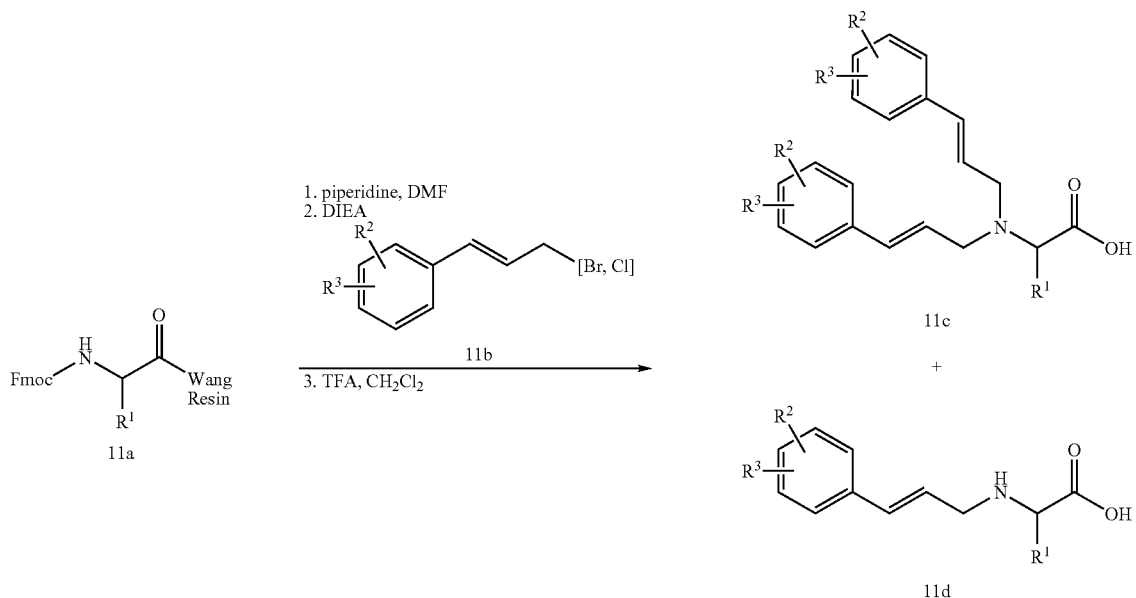

Scheme 12, Step A

An equivalent of an N-Fmoc-protected amino acid which is bound to a resin 11a is suspended in a suitable solvent such as DMF. This solvent is removed and the nitrogen protecting group (Fmoc) is removed by stirring the resin bound amino acid with an organic base, such as piperidine, and an addition portion of the solvent. After filtration and washing with solvent, the resin is suspended in an appropriate solvent such as trimethyl orthoformate (TMOF), an appropriately substituted aldehyde 12a (5 equivalents) is added, and the mixture is shaken under $N_2$ overnight. This mixture is treated with a suspension of $NaBH(OAc)_3$ (5 equivalents) in $CH_2Cl_2$ and shaken under $N_2$ overnight. After filtration and washing with a suitable solvent, the resulting product, resin bound Nα-monosubstituted amino acid 12b, is suspended and shaken in an acidic solution, such as 50% $TFA/CH_2Cl_2$, over several hours to cleave the acid from the resin to give the Nα-cinnamyl amino acid 11d.

Scheme 12, Step B

The resin 12b is suspended in an appropriate solvent such as DMF and is filtered. The appropriately substituted halide 12c and an appropriate base such as DIEA are added with some additional solvent and the mixture is shaken under $N_2$ for 18-36 h. The resin bound Nα,Nα-cinnamyl amino acid 12d is isolated from the suspension and the resin is cleaved with an acidic solution as described above to give the free acid 12e.

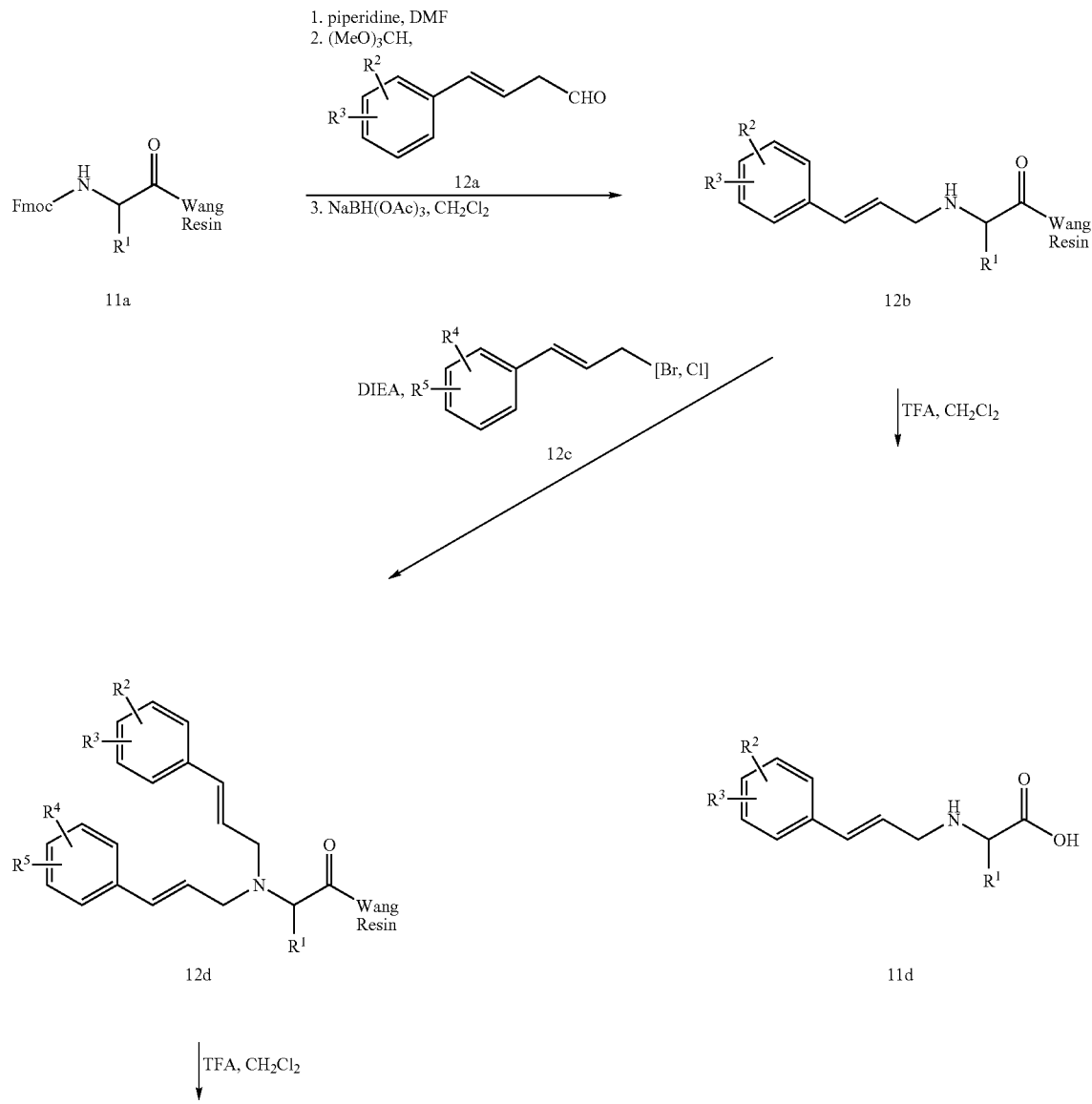

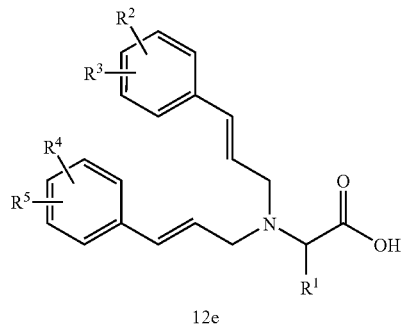

12e

General Procedure for the Solution-Phase Synthesis of Nα,Nα-Bis-Cinnamyl Amino Acids and Nα-Cinnamyl Amino Acids Scheme 13

A solution of of amino acid ester 13a, an appropriately substituted halide 11b, and an appropriate base such as DIEA, $Na_2CO_3$, or $Cs_2CO_3$ in a suitable solvent, such as DMF, is heated at 50-100° C. under $N_2$ overnight, or until the starting material is exhausted, to give a mixture of the Nα,Nα-bis-cinnamyl amino acid ester 13b and Nα-cinnamyl amino acid ester 13c. If the side chain of $R^1$ contains an acid-cleavable protecting group such as t-butylcarbamate, t-butyl ester, or t-butyl ether, those groups may be cleaved by, treatment with an acidic solution such as 30-80% TFA/$CH_2Cl_2$ or 2-4N HCl in EtOAc. For examples of 13b and 13c where the ester group $R^4$ is a primary alkyl group such as methyl or ethyl, esters 13b and 13c may be independently converted to the corresponding acids 11c and 11d by hydrolysis with an appropriate base such as aqueous NaOH, KOH, or LiOH. For examples of 13b and 13c where the ester group $R^4$ is an acid-cleavable group such as t-butyl, esters 13b and 13c may be independently converted to the corresponding acids 11c and 11d by treatment with an acidic solution such as 30-80% TFA/$CH_2Cl_2$ or 2-4N HCl in EtOAc.

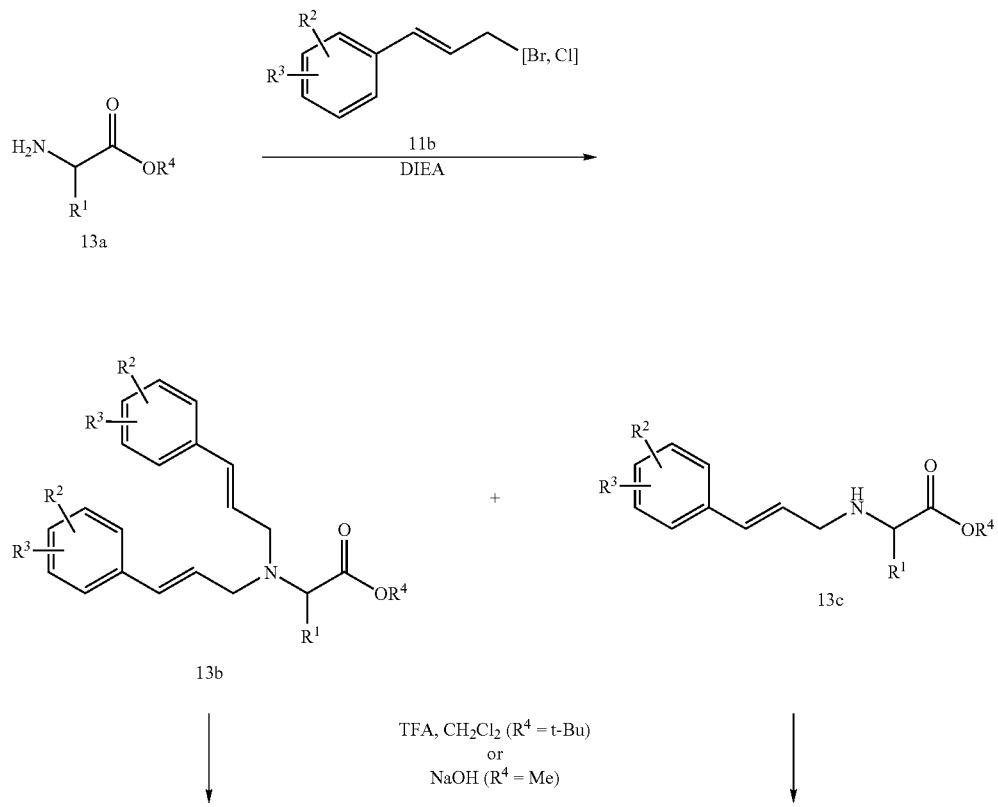

-continued

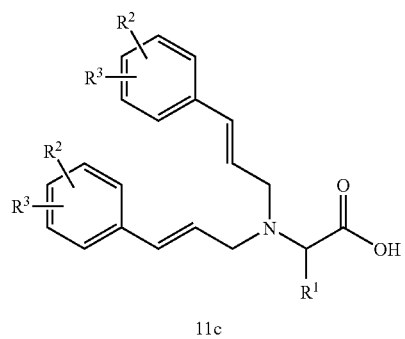

11c

+

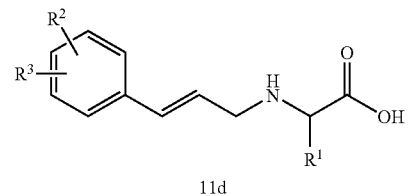

11d

Scheme 14, Step A

A solution of 1 mmol of amino acid ester and 1-1.5 mmol of the appropriately substituted aldehyde 12a in 3-5 mL of TMOF was stirred at room temperature under $N_2$ overnight. The solution was concentrated and used directly for the next reaction; optionally, the solution was partitioned between EtOAc and water, washed with brine, dried over $Na_2SO_4$, and concentrated to give crude product, which was purified by MPLC to give mono-substituted product 14a. For examples of 14a wherein the side chain $R^1$ contained an acid-cleavable protecting group such as t-butylcarbamate, t-butyl ester, or t-butyl ether, 8c was treated with an acidic solution such as 30-80% $TFA/CH_2Cl_2$ or 2-4N HCl in EtOAc. The reaction mixture was concentrated and optionally dissolved in HOAc and freeze-dried to give the deprotected form of 14a. For examples of 14a where the ester group $R^4$ is a primary alkyl group such as methyl or ethyl, esters 14a may be converted to the corresponding acids 11d by hydrolysis with an appropriate base such as aqueous NaOH, KOH, or LiOH. For examples of 14a where the ester group $R^4$ is an acid-cleavable group such as t-butyl, esters 14a may be converted to the corresponding acids 11d by treatment with an acidic solution such as 30-80% $TFA/CH_2Cl_2$ or 2-4N HCl in EtOAc.

Scheme 14, Step B

Amino ester 14a was dissolved in DMF, combined with 1.1-1.5 mmol of the appropriately substituted chloride or bromide 12c, and heated at 50-100° C. overnight. The reaction mixture was cooled and partitioned between water and EtOAc. The organic layer was washed with water and brine, dried over $Na_2SO_4$, and concentrated. The crude product was purified by MPLC to give pure 14b. For examples of 14b wherein the side chain $R^1$ contained an acid-cleavable protecting group such as t-butylcarbamate, t-butyl ester, or t-butyl ether, 8c was treated with an acidic solution such as 30-80% $TFA/CH_2Cl_2$ or 2-4N HCl in EtOAc. The reaction mixture was concentrated and optionally dissolved in HOAc and freeze-dried to give the deprotected form of 14b. For examples of 14b where the ester group $R^4$ is a primary alkyl group such as methyl or ethyl, esters 14b may be converted to the corresponding acids 12e by hydrolysis with an appropriate base such as aqueous NaOH, KOH, or LiOH. For examples of 14b where the ester group $R^4$ is an acid-cleavable group such as t-butyl, esters 14b may be converted to the corresponding acids 12e by treatment with an acidic solution such as 30-80% $TFA/CH_2Cl_2$ or 2-4N HCl in EtOAc.

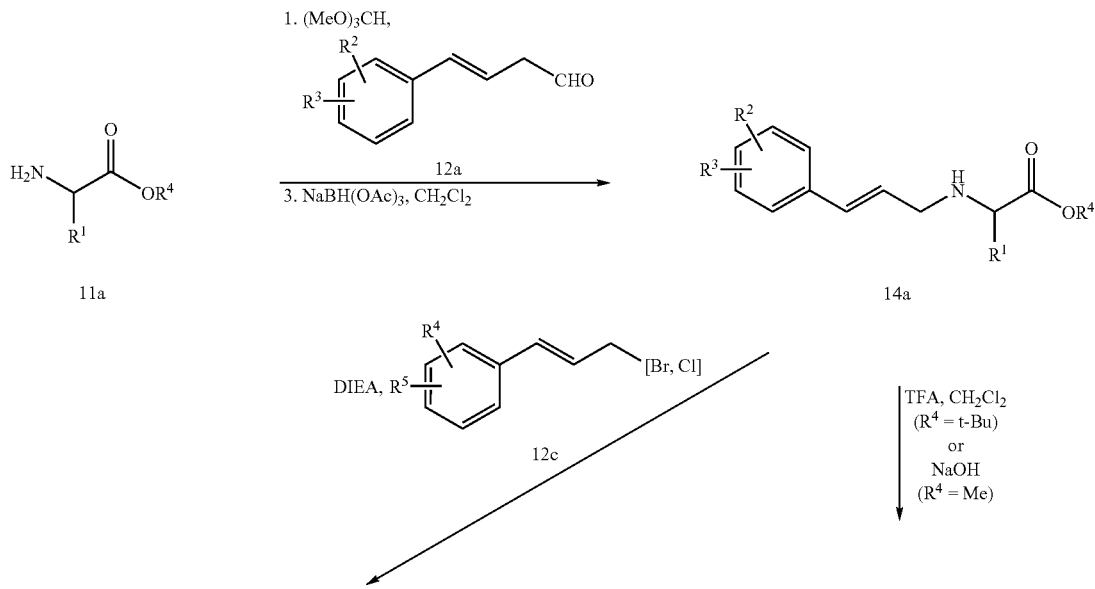

Scheme 14.

-continued
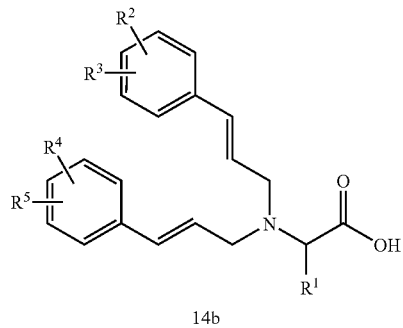
14b
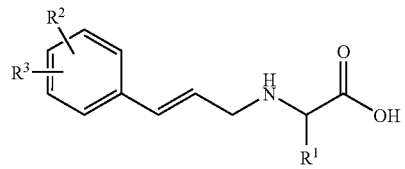
11d
TFA, CH$_2$Cl$_2$
(R$^4$ = t-Bu)
or
NaOH
(R$^4$ = Me)
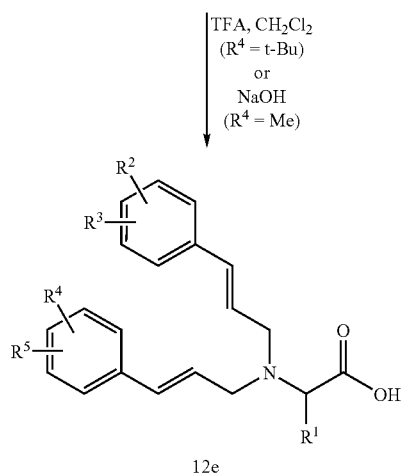
12e
Although the claimed compounds are useful as competitive binders to the EPO receptor, some compounds are more active than others and are either preferred or particularly preferred.
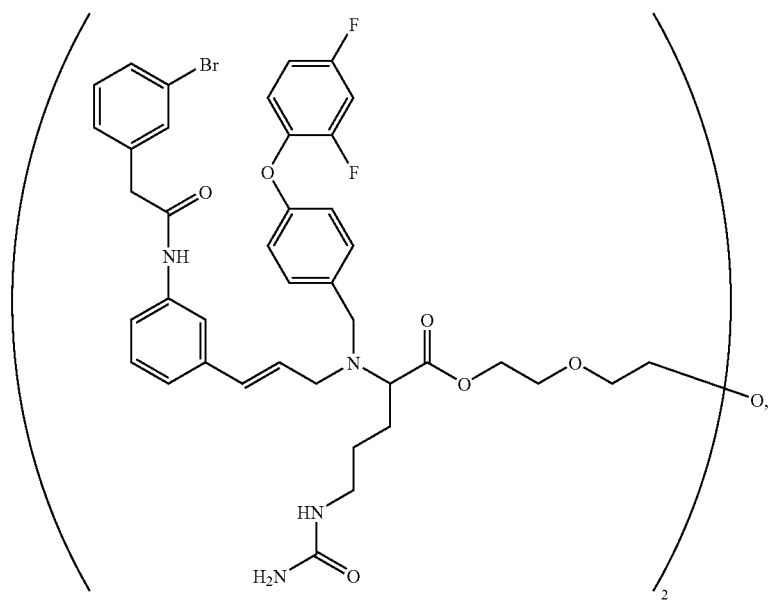

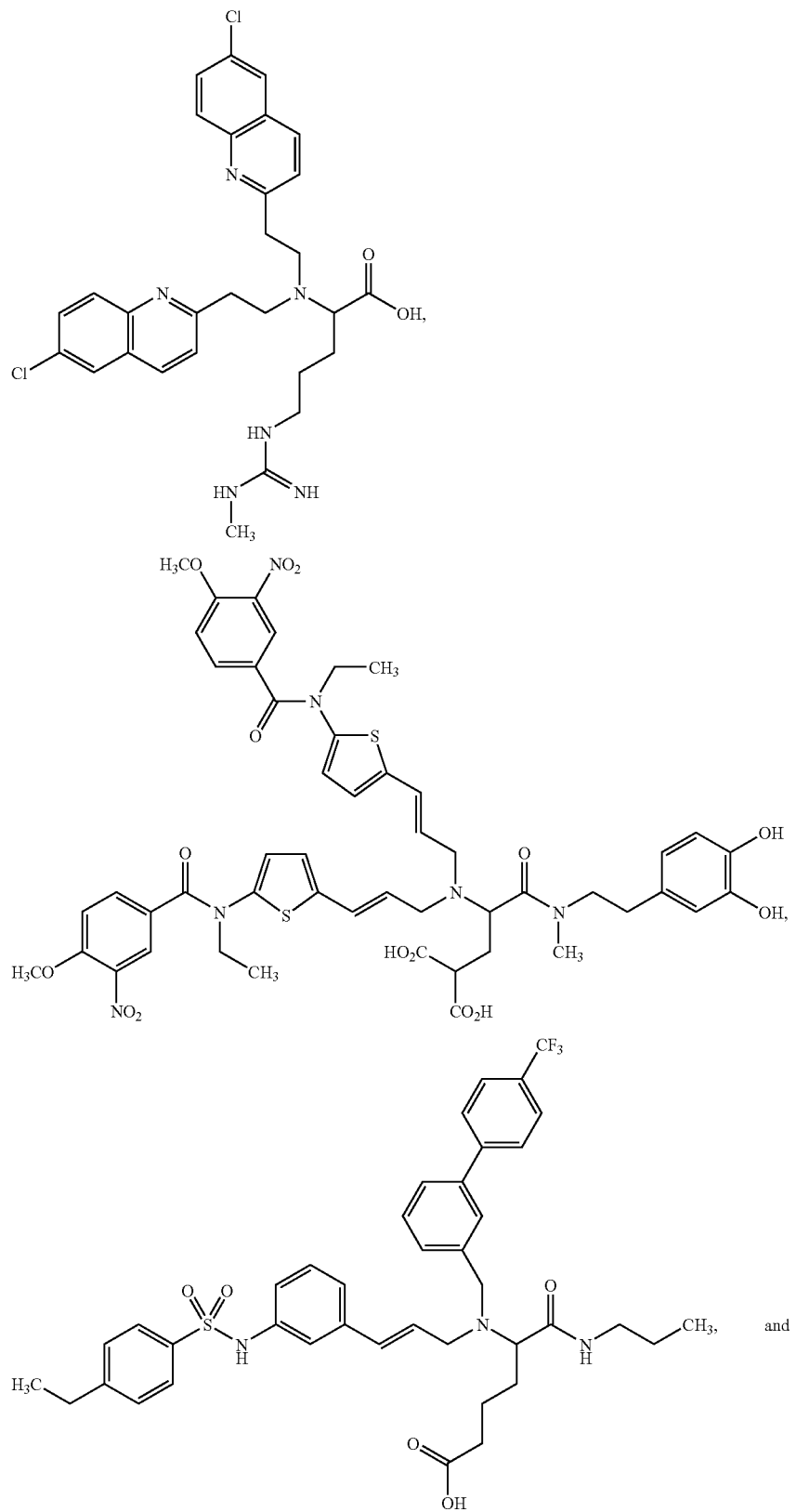

-continued

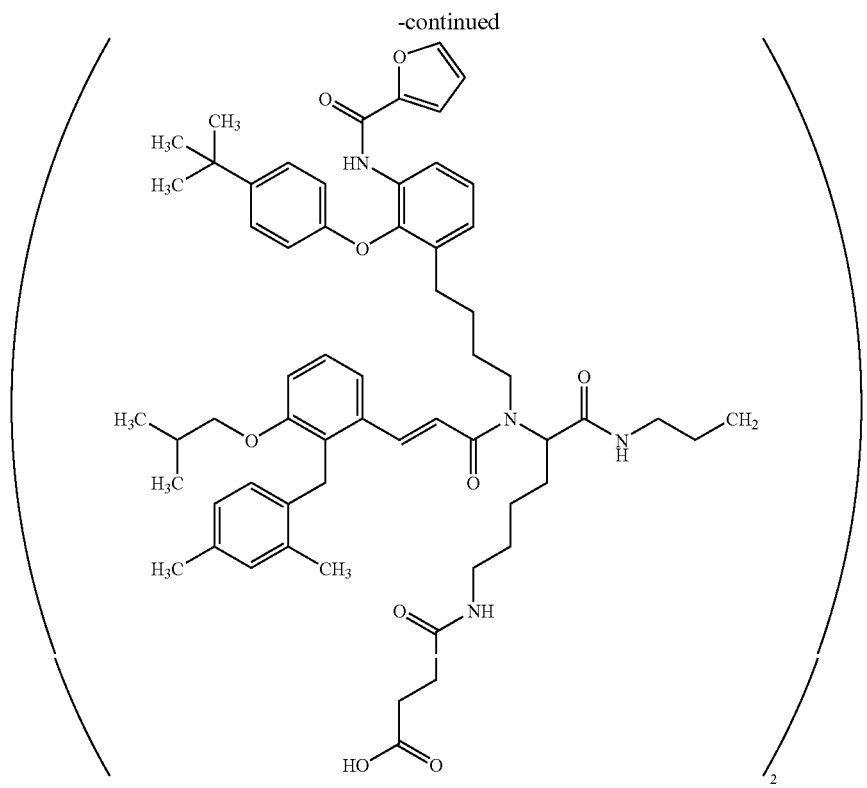

The particularly preferred "$R^1$"s are the side chain of lysine, ornithine, arginine, aspartic acid, glutamic acid, glutamine, cysteine, methionine, serine, and threonine.

The particularly preferred "$R^2$ and $R^3$" s are phenoxy, substituted phenoxy, benzyloxy, and substituted benzyloxy.

The particularly preferred "$R^4$ and $R^5$" s are phenoxy, substituted phenoxy, benzyloxy, and substituted benzyloxy.

The particularly preferred "W" is —CH=CH—

The particularly preferred "Q" is —CH=CH—

The particularly preferred "X" are $C_{1-5}$alkenyl and $CH_2$.

The particularly preferred "Y" are $C_{1-5}$alkenyl and $CH_2$.

The particularly preferred "n" are 1 and 2.

The particularly preferred "Z" are hydroxy, methoxy, phenethylamino, substituted phenethylamino, and —NH $(CH_2)_2O(CH_2)_2O(CH_2)_2NH$—.

Pharmaceutically useful compositions the compounds of the present invention, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the compound of the present invention.

Therapeutic or diagnostic compositions of the invention are administered to an individual in amounts sufficient to treat or diagnose disorders in which modulation of EPO receptor-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, transdermal, oral and parenteral.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds disclosed herein may be used alone at appropriate dosages defined by routine testing in order to obtain optimal inhibition of the EPO receptor or its activity while minimizing any potential toxicity. In addition, co-administration or sequential administration of other agents may be desirable.

The present invention also has the objective of providing suitable topical, transdermal, oral, systemic and parenteral pharmaceutical formulations for use in the novel methods of treatment of the present invention. The compositions containing compounds according to this invention as the active ingredient for use in the modulation of EPO receptors can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by transdermal delivery or injection. Likewise, they may also be administered in intravenous (both bolus and infusion), intraperitoneal, subcutaneous, topical with or without occlusion, transdermal, or intramuscular form, all using forms well known to those of ordinary skill in the pharmaceutical arts. The compounds of the present invention may be delivered by a wide variety of mechanisms, including but not limited to, transdermal delivery, or injection by needle or needle-less injection means. An effective but non-toxic amount of the compound desired can be employed as an EPO receptor modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the EPO receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacrylamidephenol, polyhydroxy-ethylaspartamidephenol, or polyethyleneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels, and other suitable polymers known to those skilled in the art.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraruminal, intratracheal, or subcutaneous, either by needle or needle-less means. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators.

The compounds of Formula I may be used in pharmaceutical compositions to treat patients (humans and other mammals) with disorders or conditions associated with the production of erythropoietin or modulated by the EPO receptor. The compounds can be administered in the manner of the commercially available product or by any oral or parenteral route (including but not limited to, intravenous, intraperitoneal, intramuscular, subcutaneous, dermal patch), where the preferred route is by injection. When the method of administration is intravenous infusion, compound of Formula I may be administered in a dose range of about 0.01 to 1 mg/kg/min. For oral administration, the dose range is about 0.1 to 100 mg/kg.

The pharmaceutical compositions can be prepared using conventional pharmaceutical excipients and compounding techniques. Oral dosage forms may be used and are elixirs, syrups, capsules, tablets and the like. Where the typical solid carrier is an inert substance such as lactose, starch, glucose, methyl cellulose, magnesium stearate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

Typically the compounds of Formula I are isolated as the free base, however when possible pharmaceutically acceptable salts can be prepared. Examples of such salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic.

In order to illustrate the invention the following examples are included. These examples do not limit the invention. They are only meant to suggest a method of practicing the invention. Those knowledgeable in chemical synthesis and the treatment of EPO related disorders may find other methods of practicing the invention. However those methods are deemed to be within the scope of this invention.

BIOLOGICAL EXAMPLES

The compounds of the invention were evaluated for the ability to compete with EPO in the following immobilized EPO receptor preparation (EBP-Ig, EPO binding protein-Ig).

EBP-Ig fusion protein (as disclosed in WO97/27219 which is herein incorporated by reference) was purified by affinity chromatography from the conditioned media of NSO cells engineered to express a recombinant gene construct which functionally joined the N-terminal 225 amino acids of the human EPO receptor and an Ig heavy chain as described herein. The interaction of biotin and streptavidin is frequently employed to capture and effectively immobilize reagents useful in assay protocols and has been employed here as a simple method to capture and immobilize EBP-Ig. EBP-Ig is initially randomly modified with an amine reactive derivative of biotin to produce biotinylated-EBP-Ig. Use of streptavidin coated plates allows the capture of the biotinylated EBP-Ig on the surface of a scintillant impregnated coated well (Flash plates, NEN-DuPont). Upon binding of [$^{125}$I]EPO to the ligand binding domain, specific distance requirements are satisfied and the scintillant is induced to emit light in response to the energy emitted by the radioligand. Unbound radioligand does not produce a measurable signal because the energy from the radioactive decay is too distant from the scintillant. The amount of light produced was quantified to estimate the amount of ligand binding. The specific assay format was suitable for the multi-well plate capacity of a Packard TopCount Microplate Scintillation counter. Compounds which were capable of reducing the amount of detected signal through competitive binding with the radioligand were identified.

Biotinylated EBP-Ig was prepared as follows. EBP-Ig (3 mL, $OD_{280}$ 2.9) was exchanged into 50 mM sodium bicarbonate, pH 8.5 using a Centriprep 10 ultrafiltration device. The final volume of the exchanged protein was 1.2 mL ($OD_{280}$ 2.6, representing about 2 mg total protein). 10 µL of a 4 mg/ml solution of NHS-LC-Biotin (Pierce) was added and the reaction mixture placed on ice in the dark for two hours. Unreacted biotin was removed by exchange of the reaction buffer into PBS in a Centriprep 10 device and the protein reagent aliquoted and stored at −70° C.

Each individual binding well (200 µL) contained final concentrations of 1 µg/mL of biotinylated EBP-Ig, 0.5 nM of [$^{125}$I]EPO (NEN Research Products, Boston, 100 µCi/µg) and 0-500 µM of test compound (from a 10-50 mM stock in 100% DMSO). All wells were adjusted to a final DMSO concentration of 5%. All assay points were performed in triplicate and with each experiment a standard curve for unlabelled EPO was performed at final concentration of 2000, 62, 15, 8, 4, and 0 nM. After all additions were made, the plate was covered with an adhesive top seal and placed in the dark at room temperature overnight. The next day all liquid was aspirated from the wells to limit analyte dependent quench of the signal, and the plates were counted on a Packard TOPCOUNT Microplate Scintillation Counter. Non-specific binding (NSB) was calculated as the mean CPM of the 2000 nM EPO wells and total binding (TB) as the mean of the wells with no added unlabelled EPO. Corrected total binding (CTB) was calculated as: TB−NSB=CTB. The concentration of test compound which reduced CTB to 50% was reported as the $IC_{50}$. Typically the $IC_{50}$ value for unlabelled EPO was ca. 2-7 nM and EMP1 was 0.1 µM. Table 1 lists the average % inhibition, and if determined the $IC_{50}$ and $IC_{30}$ values for compounds of Formula I, where the compound numbers refer to the compounds in the tables accompanying the preparative examples.

TABLE 1

Inhibition of EPO binding to EBP-Ig

| cpd | % inh @ 50 µM | $IC_{30}$ µM* | $IC_{50}$, µM* |
|---|---|---|---|
| 11 | 70 | nd | nd |
| 12 | 59 | nd | nd |
| 14 | 30 | nd | nd |
| 15 | 48 | nd | nd |
| 77 | 52 | 30 | 40 |
| 82 | 32 | nd | nd |
| 86 | 37 | nd | nd |
| 100 | 34 | nd | nd |
| 101 | 32 | nd | nd |
| 104 | 78 | 10 | 30 |
| 105 | 70 | 25 | 35 |
| 107 | 78 | 30 | 42 |
| 108 | 81 | 23 | 36 |
| 110 | 54 | 6 | 10 |
| 112 | 59 | 2 | 10 |
| 114 | 37 | 10 | nd |
| 115 | 35 | nd | nd |
| 116 | 32 | nd | nd |
| 117 | 34 | nd | nd |
| 118 | 36 | 2 | 10 |
| 119 | 34 | nd | nd |
| 120 | 35 | nd | nd |
| 121 | 45 | 6 | nd |
| 137 | 60 | 5 | 30 |
| 139 | 46 | 2 | 10 |
| 178 | 36 | nd | nd |
| 179 | 30 | nd | nd |
| 183 | 36 | nd | nd |
| 184 | 53 | 10 | nd |
| 203 | 37 | 50 | nd |
| 211 | 62 | 20 | 65 |
| 220 | 45 | 30 | 50 |
| 221 | 48 | 10 | 80 |
| 222 | 56 | 5 | nd |
| 224 | 51 | 25 | 50 |
| 227 | 48 | 20 | 50 |
| 230 | 42 | nd | nd |
| 231 | 36 | nd | nd |
| 235 | 49 | 20 | 50 |
| 237 | 55 | 30 | 70 |
| 238 | 39 | nd | nd |
| 239 | 46 | 8 | 50 |
| 243 | 75 | 2 | 18 |
| 244 | 66 | 1 | 28 |
| 246 | 79 | 10 | 75 |
| 247 | 47 | 7 | 18 |
| 248 | 56 | 7 | 20 |
| 249 | 72 | 7 | 10 |
| 250 | 78 | 7 | 20 |
| 251 | 49 | 10 | 45 |
| 261 | 51 | 1.5 | 2 |
| 262 | 93 | 1 | 1.5 |
| 263 | 88 | 1 | 1.5 |
| 264 | 89 | 1.5 | 8 |
| 265 | 65 | 1 | 6 |
| 266 | 82 | 1 | 4 |
| 267 | 83 | 2 | 6 |
| 268 | 40 | nd | nd |
| 269 | 55 | 8 | 85 |
| 270 | 56 | 7 | 100 |
| 271 | 77 | 2 | 7 |
| 272 | 78 | 5 | 10 |
| 285 | 41 | nd | nd |
| 286 | 46 | 35 | 65 |
| 287 | 36 | nd | nd |
| 300 | 57 | 35 | 145 |
| 305 | 48 | 35 | 225 |
| 312 | 45 | 10 | 85 |
| 321 | 42 | 45 | nd |
| 363 | 33 | 35 | 220 |
| 366 | 38 | 65 | nd |
| 368 | 40 | 90 | nd |

*nd = not determined

PREPARATIVE EXAMPLES

Unless otherwise noted, materials used in the examples were obtained from commercial supplies and were used without further purification. Melting points were determined on a Thomas Hoover apparatus and are uncorrected. Proton nuclear magnetic resonance ($^1$H NMR) spectra were measured in the indicated solvent with tetramethylsilane (TMS) as the internal standard using a Bruker AC-300 NMR spectrometer. NMR chemical shifts are expressed in parts per million (ppm) downfield from internal TMS using the d scale. $^1$H NMR data are tabulated in order; multiplicity, (s, singlet; d, doublet; t, triplet; q, quartet; m, multiplet), number of protons, coupling constant in Hertz). Electrospray (ES) mass spectra (MS) were determined on a Hewlett Packard Series 1090 LCMS Engine. Elemental analyses were performed by Quantitative Technologies, Inc. (QTI), PO Box 470, Salem Industrial Park, Bldg #5, Whitehouse, N.J. 08888-0470. Analytical thin layer chromatography (TLC) was done with Merck Silica Gel 60 $F_{254}$ plates (250 micron). Medium pressure liquid chromatography (MPLC) was done with Merck Silica Gel 60 (230-400 mesh).

Example 1

N,N-bis(3-Phenoxycinnamyl)Glu(O-t-Bu)-OMe (cpd 96) and N-(3-phenoxycinnamyl)Glu(O-t-Bu)-OMe (cpd 334)

A solution of 500 mg (1.97 mmol) of H-Glu(O-t-Bu)OMe.HCl, 997 mg (3.45 mmol) of 3-phenoxycinnamyl bromide (Jackson, W. P.; Islip, P. J.; Kneen, G.; Pugh, A.; Wates, P. J. *J.Med.Chem.* 31 1988; 499-500), and 0.89 mL (5.1 mmol, 660 mg) of DIEA in 5 mL of DMF was stirred under $N_2$ at room temperature for 40 h. The mixture was partitioned between EtOAc and water and the organic layer was washed with water and brine. After drying over $Na_2SO_4$, the organic solution was concentrated to give 1.24 g of orange oil. The crude residue was purified by MPLC using a solvent gradient ranging from 10-30% EtOAc/hexanes to give two products. The less polar product (cpd 96, 235 mg, 19% based on starting amino acid), was isolated as a pale yellow oil; $^1$H NMR (CDCl$_3$, 300 MHz) 1.39 (s, 9H), 2.0 (m, 2H), 2.33 (dt, 2H, J=2, 7 Hz), 3.24 (dd, 2H, J=8, 15 Hz), 3.5, (m, 3H), 3.69 (s, 3H), 6.13 (m, 2H), 6.47 (d, 2H, J=16 Hz), 6.86 (dd, 2H, J=1.5, 8 Hz), 7.0-7.4 (complex, 16H); MS (ES+) m/z 634 (MH+).

The more polar product (cpd 334, 422 mg, 50% based on starting amino acid) was isolated as a pale yellow oil; $^1$H NMR (CDCl$_3$, 300 MHz) 1.42 (s, 9H), 1.9 (m, 2H), 2.35 (t, 2H, J=7.5 Hz), 3.2-3.4 (complex, 3H), 3.71 (s, 3H), 6.17 (dt, 1H, J=16, 6 Hz), 6.46 (d, 1H, J=16 Hz), 6.87 (dd, 1H, J=1.5, 8 Hz), 7.01 (m, 3H), 7.10 (t, 2H, J=7.5 Hz), 7.2-7.4 (complex, 3H); MS (ES+) m/z 426 (MH+). Anal. Calcd for $C_{25}H_{31}NO_5$: C, 70.57; H, 7.34; N, 3.29. Found: C, 70.29; H, 7.14; N, 3.08.

Example 2

N-(3-Phenoxycinnamyl)Glu-OMe (cpd 325)

A solution of 95 mg (0.22 mmol) of N-(3-phenoxycinnamyl)Glu(O-t-Bu)-OMe (cpd 334) in 3 mL of 50% TFA/CH$_2$Cl$_2$ was stirred for 2 h at room temperature. The mixture was concentrated and the residue was dissolve in acetic acid and freeze-dried to give 117 mg of N-(3-phenoxycinnamyl) Glu-OMe (cpd 325) as an off-white solid; $^1$H NMR (CD$_3$OD, 300 MHz) 2.3-2.7 (complex, 4H), 3.78 (s, 3H), 3.81 (d, 2H, J=7 Hz), 4.09 (t, 1H, J=5 Hz), 6.17 (dt, 1H, J=16, 7 Hz), 6.55 (d, 1H, J=16 Hz), 6.9 (m, 4H), 7.11 (t, 2H, J=7.5 Hz), 7.3 (m, 4H); MS (ES+) m/z 370 (MH+), 209. Anal. Calcd for $C_{21}H_{23}NO_5 \cdot C_2HF_3O_2$: C, 57.14; H, 5.00; N, 2.90. Found: C, 57.07; H, 5.02; N, 2.73.

Example 3

N,N-bis(3-Phenoxycinnamyl)Asp(O-t-Bu)-O-t-Bu (cpd 106)

A solution of 1.00 g (3.55 mmol) of Asp(O-t-Bu)-O-t-Bu.HCl, 2.05 g (7.1 mmol) of 3-phenoxycinnamyl bromide, and 1.86 mL (10.7 mmol, 1.38 g) of DIEA in 15 mL of DMF was heated under N$_2$ at 60° C. overnight. Additional 3-phenoxycinnamyl bromide (1.0 g, 3.4 mmol) and DIEA (0.95 mL, 0.705 g, 5.4 mmol) were added and heating was continued for an additional 14 h. The mixture was cooled and partitioned between EtOAc and water. The organic layer was washed twice with water, once with brine, and was dried over Na$_2$SO$_4$. The solution was concentrated to give 3.5 g of an amber oil which was purified by MPLC using a solvent gradient ranging from 2.5-3% EtOAc/hexanes to afford 1.21 g of cpd 106 as a pale yellow oil; $^1$H NMR (CDCl$_3$, 300 MHz) 1.41 (s, 9H), 1.48 (s, 9H), 2.49 (dd, 1H, J=7.5, 15.5 Hz), 2.70 (dd, 1H, J=7.5, 15.5 Hz), 3.26 (dd, 2H, J=7.5, 14.5 Hz), 3.47 (dd, 2H, J=4, 14.5 Hz), 3.88 (t, 1H, J=7.5), 6.13 (m, 2H), 6.48 (d, 2H, J=16 Hz), 6.86 (dd, 2H, J=2, 8 Hz), 7.0 (m, 6H), 7.1 (m, 4H), 7.2-7.4 (complex, 6H); MS (ES+) m/z 662 (MH+).

Example 4

N,N-bis(3-Phenoxycinnamyl)Asp-OH (cpd 107)

A solution of 1.14 g (1.62 mmol) of cpd 106 in 16 mL of 50% TFA/CH$_2$Cl$_2$ was stirred at room temperature for 24 h. The solution was concentrated and pumped to give 1.37 g (~100%) cpd 107 as an amber oil; $^1$H NMR (CDCl$_3$, 300 MHz) 3.1 (m, 2H), 4.0 (dd, 2H, J=8, 14 Hz), 4.27 (dd, 2H, J=8, 16 Hz), 4.70 (t, 1H, J=4 Hz), 6.38 (2H, dt, J=16, 8 Hz), 6.7-7.4 (complex, 20H); MS (ES−) m/z 562 ([M-H]+).

Example 5

N,N-bis(4-Benzyloxybenzyl)Lys(Boc)-OMe (cpd 111) and N-(4-Benzyloxybenzyl)Lys(Boc)-OMe A solution of 594 mg (2.0 mmol) of Lys(Boc)-OMe.HCl, 524 mg (2.25 mmol) of 4-benzyloxybenzyl chloride, 75 mg (0.5 mmol), of NaI, and 0.61 mL (3.5 mol, 452 mg) of DIEA was warmed at 50-70° C. under N$_2$ overnight. The mixture was cooled and partioned between EtOAc and water. The organic layer was washed twice with water, once with brine, and was dried over Na$_2$SO$_4$. The organic solution was concentrated to give 0.83 g of amber oil which was purified by MPLC using a solvent gradient ranging from 15-40% EtOAc/hexanes to give two products. The less polar product (296 mg), cpd 111, was isolated as a pale yellow oil; $^1$H NMR (CDCl$_3$, 300 MHz) 1.28 (m, 4H), 1.43 (s, 9H), 1.70 (m, 2H), 3.03 (m, 2H), 3.28 (t, 1H, J=7 Hz), 3.40 (d, 2H, J=13.5 Hz), 3.74 (s, 3H), 3.81 (d, 2H, J=13.5 Hz), 5.05 (2, 4H), 6.92 (d, 4H, J=8.5), 7.23 (d, 4H, J=8.5), 7.25-7.5 (complex, 10H); MS (ES+) m/z 653 (MH+).

The more polar product (406 mg), N-(4-benzyloxybenzyl) Lys(Boc)-OMe, was isolated as a white solid; $^1$H NMR (CDCl$_3$, 300 MHz) 1.4 (, 4H), 1.43 (s, 9H), 1.65 (m, 3H), 3.08 (m, 2H), 3.23 (t, 1H, J=6.5 Hz), 3.54 (d, 1H, J=12.5 Hz), 3.71 (s, 3H), 3.73 (d, 1H, J=12.5 Hz), 5.05 (s, 2H), 6.92 (d, 2H, J=8.5 Hz), 7.23 (d, 2H, J=8.5 Hz), 7.25-7.5 (complex, 5H); MS (ES+) m/z 457 (MH+).

Example 6

N-(4-Benzyloxybenzyl)-N-(3-nitrobenzyl)Lys(Boc)-OMe (cpd 113)

A solution of 374 mg (0.82 mmol) of N-(4-Benzyloxybenzyl)Lys(Boc)-OMe, 221 mg (1.03 mmol) of 4-nitrobenzyl bromide, and 197 L (1.13 mmol, 146 mg) of DIEA was warmed at 50-70° C. for 4 h, then at 40-50° C. overnight. After the addition of 0.2 mL of 1N aqueous HCl, the mixture was partioned between EtOAc and water. The organic layer was washed twice with water, once with brine, and was dried over Na$_2$SO$_4$. The organic solution was concentrated to give 610 mg of an amber oil which was purified by MPLC 1:3 EtOAc/hexanes to afford 436 mg (90%) cpd 113 as a pale yellow oil; $^1$H NMR (CDCl$_3$, 300 MHz) 1.35 (m, 4H), 1.42 (s, 9H), 1.75 (broad q, 2H, J=8 Hz), 3.06 (broad q, 2H, J=6 Hz), 3.28 (t, 1H, J=7.5 Hz), 3.48 (d, 1H, J=13.5 Hz), 3.66 (d, 1H, J=14.5 Hz), 3.76 (s, 3H), 3.79 (d, 1H, J=13.5 Hz), 3.97 (d, 1H, J=14.5 Hz), 4.47 (broad s, 1H), 5.05 (s, 2H), 6.93 (d, 2H, J=8.5 Hz), 7.22 (d, 2H, J=8.5 Hz), 7.3-7.5 (complex, 6H), 7.65 (d, 1H, J=7.5 Hz), 8.09 (d, 1H, J=8 Hz), 8.22 (s, 1H); MS (ES+) m/z 592 (MH+).

Example 7

N-(3-Aminobenzyl)-N-(4-benzyloxybenzyl)Lys (Boc)-OMe

A solution of 361 mg (0.61 mmol) of cpd 113 and 835 mg (3.7 mmol) of SnCl$_2$ dihydrate was stirred under N$_2$ at room temperature for 6 h. The slightly cloudy mixture was poured into 200 mL of 5% aqueous Na$_2$CO$_3$ with rapid stirring. The resulting milky suspension was extracted with three 75 mL portions of CH$_2$Cl$_2$ and the combined organic layers were washed with brine and dried over Na$_2$SO$_4$. The extracts were concentrated to give 344 mg of colorless oil which was purified by MPLC using 1:2 EtOAc/hexanes to provide 291 mg of N-(3-aminobenzyl)-N-(4-benzyloxybenzyl)Lys(Boc)-OMe as a yellow oil; $^1$H NMR (CDCl$_3$, 300 MHz) 1.25 (m, 4H), 1.44 (s, 9H), 1.70 (m, 2H), 3.31 (dd, 1H, J=6, 9 Hz), 3.38 (d, 1H, J=7 Hz), 3.40 (d, 1H, J=13.5 Hz), 3.74 (s, 3H), 3.81 (d, 1H, J=14 Hz), 3.83 (d, 1H, J=13.5 Hz), 4.52 (broad s, 1H), 5.05 (s, 2H), 6.50 (broad d, 1H, J=8 Hz), 6.70 (m, 2H), 6.92 (d, 2H, J=8.5 Hz), 7.08 (t, 1H, J=7.5 Hz), 7.2-7.5 (complex, 7H); MS (ES+) m/z 562 (base, MH+), 506.

Example 8

N-(4-Benzyloxybenzyl)-N-(3-((2-furancarbonyl)amino)benzyl)Lys-OMe (cpd 117)

A solution of 42 mg (0.075 mmol) of N-(3-aminobenzyl)-N-(4-benzyloxybenzyl)Lys(Boc)-OMe and 12 μL (12 mg, 0.15 mmol) of pyridine in 0.5 mL of 1,2-dichloroethane was combined with 8.1 μL (11 mg, 0.083 mmol) and stirred under N$_2$ overnight. EtOAc (3 mL) was added and the solution was washed twice with 2 mL of water and 2 mL of saturated aqueous NaHCO$_3$. The EtOAc solution was filtered through a pad of Na$_2$SO$_4$ and concentrated to give 44 mg of N-(4-benzyloxybenzyl)-N-(3-((2-furancarbonyl)amino)benzyl)Lys(Boc)-OMe; MS (ES+) m/z 356 (MH+). The Boc-protected intermediate was stirred in 2 mL of 50% TFA/CH$_2$Cl$_2$ for 2 h and was concentrated and pumped at high vacuum to provide 66 mg of cpd 117 as the bis-TFA salt; $^1$H NMR (CD$_3$OD, 300 MHz) 1.55 (m, 2H), 1.65 (m, 2H), 2.10 (m, 2H), 2.93 (t, 2H, J=7 Hz), 3.68 (t, 1H, J=7 Hz), 3.78 (s, 3H), 4.20 (m, 4H), 5.09 (s, 2H), 6.66 (dd, 1H, J=1.5, 3.5 Hz), 7.03 (d, 2H, J=8.5 Hz), 7.1-7.6 (complex, 11H), 7.76 (m, H) 8.07 (m, 1H); MS (ES+) m/z 556 (base, MH+), 360, 197.

Example 9

N,N-bis(3-Nitrobenzyl)Asp(O-t-Bu)-O-t-Bu (cpd 62)

A solution of 0.50 mg (1.77 mmol) of Asp(O-t-Bu)-Ot-Bu.HCl, 1.17 g (5.42 mmol) of 3-nitrobenzyl bromide, and 1.25 mL (0.93 g, 7.2 mmol) of DIEA in 6 mL of DMF was stirred at room temperature under N$_2$ for 24 h and was heated at 70-80° C. overnight. The reaction mixture was partitioned between EtOAc and water and the organic layer was washed twice with water and once with brine. After drying over Na$_2$SO$_4$, the organic solution was concentrated to give 0.86 g of a yellow oil which was purified by MPLC using 1:9 EtOAc/hexanes to afford 0.849 g (93%) cpd 62 as a pale yellow oil; $^1$H NMR (CDCl$_3$, 300 MHz) 1.43 (s, 9H), 1.57 (s, 9H), 2.59 (dd, 1H, J=7.5, 16 Hz), 2.76 (dd, 1H, J=7, 16 Hz), 3.72 (t, 1H, J=7.5 Hz), 3.78 (d, 2H, J=14 Hz), 3.92 (d, 2H, J=14 Hz), 7.47 (t, 2H, J=8 Hz), 7.67 (d, 2H, J=7.5 Hz), 8.09 (broad d, 2H J=8 Hz), 8.16 (broad s, 2H); MS (ES+) m/z 538 (MNa+), 516 (base, MH+), 460, 404, 237.

Example 10

N,N-bis(3-Aminobenzyl)Asp(O-t-Bu)-O-t-Bu

A solution of 0.644 g (1.25 mmol) of cpd 62 and 2.82 g (12.5 mmol) of SnCl$_2$.2H$_2$O in 12 mL of absolute EtOH was refluxed for 1.5 h. The mixture was cooled and poured into 300 mL of 5% aqueous Na$_2$CO$_3$ with rapid stirring. The cloudy mixture was extracted with three 150 mL portions of CH$_2$Cl$_2$ and the organic extracts were washed with brine and dried over Na$_2$SO$_4$. The CH$_2$Cl$_2$ solution was concentrated to afford 210 mg (37%) of N,N-bis(3-aminobenzyl)Asp(O-t-Bu)-O-t-Bu as a cloudy yellow oil which was used without purification; $^1$H NMR (CDCl$_3$, 300 MHz) 1.40 (s, 9H), 1.52 (s, 9H), 2.48 (dd, 1H, J=7, 16 Hz), 2.76 (dd, 1H, J=8, 16 Hz), 3.48 (d, 2H, J=14 Hz), 3.55 (m, 1H), 3.73 (d, 2H, J=14 Hz), 6.56 (broad d, 2H J=8 Hz), 6.70 (broad s, 2H), 6.77 (d, 2H, J=7.5 Hz), 7.08 (t, 2H, J=8 Hz); MS (ES+) m/z 478 (MNa+), 456 (base, MH+), 400, 344.

Example 11

N,N-bis(3-(4-Methylbenzoyl)aminobenzyl)Asp(O-t-Bu)-O-t-Bu

To a solution of 109 mg (0.24 mmol) of N,N-bis(3-aminobenzyl)Asp(O-t-Bu)-O-t-Bu, 29 mg (0.24 mmol) of DMAP, 125 μL (93 mg, 0.72 mmol) of DIEA in 1 mL of CH$_2$Cl$_2$ was added 95 μL (111 mg, 0.72 mmol) of 4-methylbenzoyl chloride. The solution was stirred under N$_2$ overnight and was then partitioned between EtOAc and water. The organic layer was washed with saturated aqueous NaHCO$_3$ and brine, dried over Na$_2$SO$_4$, and concentrated to give 177 mg of yellow oil. The crude material was purified by MPLC using a solvent gradient ranging from 20-25% EtOAc/hexanes to provide 87 mg of N,N-bis(3-(4-methylbenzoyl)aminobenzyl)Asp(O-t-Bu)-O-t-Bu as a pale yellow oil; $^1$H NMR (CDCl$_3$, 300 MHz) 1.36 (s, 9H), 1.55 (s, 9H), 2.35 (s, 6H), 2.53 (dd, 1H, J=6, 16 Hz), 2.76 (dd, 1H, J=9, 16 Hz), 3.69 (d, 2H, J=14), 3.77 (dd, 1H, J=6, 9 Hz), 3.83 (d, 2H, J=14), 7.01 (m, 6H), 7.26 (t, 2H, J=8 Hz), 7.59 (m, 6H), 8.11 (s, 2H), 8.49 (s, 2H); MS (ES+) m/z 714 (MNa+), 692 (base, MH+), 636, 580.

Example 12

N,N-bis(3-(4-Methylbenzoyl)aminobenzyl)Asp-OH (cpd 64)

A solution of 87 mg (0.13 mmol) of N,N-bis(3-(4-methylbenzoyl)amino-benzyl)Asp(O-t-Bu)-O-t-Bu in 1 mL of 50% TFA/CH$_2$Cl$_2$ was stirred overnight. The mixture was concentrated and the residue was dissolved in HOAc and freeze-dried to afford 77 mg cpd 64 as a white solid; $^1$H NMR (CD$_3$OD, 300 MHz) 2.40 (s, 6H), 2.85 (dd, 1H, J=6, 16.5 Hz), 2.98 (dd, 1H, J=8, 16.5 Hz), 4.02 (d, 2H, J=13.5 Hz), 4.08 (d, 4H, J=13.5 Hz), 4.10 (t, 1H, J=6.5 Hz), 7.22 (m, 6H), 7.34 (t, 2H, J=7.5 Hz), 7.60 (broad d, 2H, J=9 Hz), 7.76 (d, 4H, J=8 Hz), 7.88 (broad s, 2H); MS (ES+) m/z 580 (base, MH+).

Example 13

[N-Cbz-Glu(O-t-Bu)-NHCH$_2$CH$_2$OCH$_2$]$_2$

To a solution of 1.69 g (5.0 mmol) of N-Cbz-Glu(O-t-Bu)-OH, 0.365 mL (0.371 g, 2.5 mmol) of 1,8-diamino-3,6-dioxaoctane, 0.743 g (5.5 mmol) of HOBT, and 1.05 mL (0.776 g, 6.0 mmol) of DIEA in 15 mL of CH$_2$Cl$_2$ was added 1.05 g (5.5 mmol) of EDCI in one portion. After stirring at room temperature under N$_2$ overnight, the mixture was partitioned between EtOAc and 10% aqueous citric acid. The organic layer was washed with water, saturated NaHCO$_3$, and brine, dried over Na$_2$SO$_4$, and concentrated to give 1.87 g of (N-Cbz-Glu(O-t-Bu)-NHCH$_2$CH$_2$OCH$_2$)$_2$ as a colorless oil; $^1$H NMR (CD$_3$OD, 300 MHz) 1.43 (s, 18H), 1.85 (m, 2H), 2.05 (m, 2H), 2.31 (t, 4H, J=8 Hz), 3.37 (t, 4H, J=5 Hz), 3.52 (t, 4H, J=5 Hz), 3.58 (s, 4H), 4.15 (m, 2H), 5.09 (dd, 4H, J=12, 16 Hz), 7.30 (m, 10H); MS (ES+) m/z 809 (base, MNa+), 787 (MH+).

Example 14

[Glu(O-t-Bu)-NHCH₂CH₂OCH₂]₂

Ammonium formate (0.78 g, 12.4 mmol) and 0.16 g of 10% palladium on carbon were added to a solution of (N-Cbz-Glu(O-t-Bu)-NHCH₂CH₂OCH₂)₂ in 12 mL of MeOH and the resulting suspension was stirred under N₂ at room temperature overnight. The mixture was diluted with CH₂Cl₂ and filtered through a Celite pad. The solids were washed thoroughly with CH₂Cl₂ and the combined organic filtrates were concentrated to dryness. The residue was partitioned between CH₂Cl₂ and saturated aqueous NaHCO₃, washed with brine, dried over Na₂SO₄, and concentrated to give 1.13 g of (Glu(O-t-Bu)-NHCH₂CH₂OCH₂)₂ as a colorless oil; 1.44 (s, 18H), 1.81 (m, 2H), 2.08 (m, 2H), 2.35 (m, 4H), 3.39 (dd, 2H, J=5, 7.5 Hz), 3.47 (t, 4H, J=5 Hz), 3.58 (t, 4H, J=5 Hz), 7.53 (m, 2H).

Example 15

[N,N-bis(4-Benzyloxybenzyl)Glu(O-t-Bu)-NHCH₂CH₂OCH₂]₂ (cpd 245)

A solution of 199 mg (0.384 mmol) of [Glu(O-t-Bu)-NHCH₂CH₂OCH₂]₂, 403 mg (1.73 mmol) of 4-benzyloxybenzyl chloride, 30 mg (0.2 mmol) of NaI, and 334 L (248 mg, 1.92 mmol) of DIEA was stirred under N₂ at room temperature for several days. The solution was partitioned between EtOAc and water and the organic layer was washed three times with water and once with brine. After drying over Na₂SO₄, the solution was concentrated to give 528 mg of yellow oil which was purified by MPLC using a solvent gradient ranging from 42-50% EtOAc/hexanes to afford 318 mg (64%) of cpd 245 as a white foam; ¹H NMR (CDCl₃, 300 MHz) 1.42 (s, 18H), 2.01 (m, 4H), 2.38 (m, 2H), 2.55 (m, 2H), 3.03 (dd, 2H, J=5, 8 Hz), 3.31 (m, 2H), 3.4-3.6 (complex, 18H), 4.99 (s, 8H), 6.89 (d, 8H, J=8.5), 7.1-7.4 complex, 30H).

Example 16

[N,N-bis(4-Benzyloxybenzyl)GluNHCH₂CH₂OCH₂]₂ (cpd 246)

A solution of 219 mg (0.168 mmol) of cpd 245 in 2 mL of 33% TFA/CH₂Cl₂ was stirred ad room temperature overnight. The mixture was concentrated to give a crude product which was dissolved in HOAc and freeze-dried to afford 251 mg of cpd 246 as an amber oil; ¹H NMR (CD₃OD, 300 MHz) 2.1-2.6 (complex, 8H), 3.3-3.6 (complex, 8H), 3.57 (s, 4H), 3.78 (m, 2H), 4.25 (broad d, 4H, J=14 Hz), 4.36 (broad d, 4H, J=14 Hz), 5.09 (s, 8H), 7.03 (d, 8H, J=8 Hz), 7.3-7.5 (complex, 28H); MS (ES+) m/z 1192 (MH+), 995, 596, 197 (base).

Example 17

[N-(3-Phenoxybenzyl)Glu(O-t-Bu)-NHCH₂CH₂OCH₂]2

A solution of 680 mg (0.76 mmol) of [Glu(O-t-Bu)-NHCH₂CH₂OCH₂]₂ and 278 μL (317 mg, 1.6 mmol) of 3-phenoxybenzaldehyde in 3 mL of TMOF was stirred overnight at room temperature under N₂. The mixture was concentrated and pumped at high vacuum to give a colorless oil which was dissolved in 3 mL of CH₂Cl₂ and treated with 678 mg (3.2 mmol) of NaBH(OAc)₃. After stirring under N₂ for 2 days, 50 mL of saturated aqueous NaHCO₃ was added and the mixture was extracted with CH₂Cl₂. The organic layers were combined, dried over Na₂SO₄, and concentrated and the crude product (1.01 g) was purified by MPLC using a solvent gradient ranging from 2-4% MeOH/CH₂Cl₂ to afford 490 mg of [N-(3-phenoxybenzyl)Glu(O-t-Bu)-NHCH₂CH₂OCH₂]₂ as a colorless oil; ¹H NMR (CDCl₃, 300 MHz) 1.41 (s, 18H), 1.89 (m, 4H), 2.31 (m, 4H), 3.12 (t, 2H, J=6 Hz), 3.45 (m, 8H), 3.55 (s, 4H), 3.60 (d, 2H, J=13.5 Hz), 3.73 (d, 2H, J=13.5 Hz), 6.86 (dd, 2H, J=1.5, 8 Hz), 7.00 (m, 8H), 7.2-7.4 (complex, 8H); MS (ES+) m/z 883 (MH+), 589, 442, 414, 386 (base), 183.

Example 18

[N-(3-Nitrobenzyl)-N-(3-phenoxybenzyl)-Glu(O-t-Bu)-NHCH₂CH₂OCH₂]₂

DIEA (269 μL, 199 mg, 1.54 mmol), 3-nitrobenzyl bromide (322 mg, 1.49 mmol), and [N-(3-phenoxybenzyl)Glu(O-t-Bu)-NHCH₂CH₂OCH₂]₂ (482 mg, 0.546 mmol) were combined in 2 mL of DMF and heated at 60-70° C. under N₂ for 2 days. The reaction mixture was cooled and partitioned between 100 mL of EtOAc and water. The organic layer was washed with three times with water and once with brine, dried over Na₂SO₄, and concentrated to give 661 mg (~100%) of [N-(3-nitrobenzyl)-N-(3-phenoxybenzyl)-Glu(O-t-Bu)-NHCH₂CH₂OCH₂]₂ which was used without purification; MS (ES+) m/z 1154 (MH+), 577, 130 (base).

Example 19

[N-(3-Aminobenzyl)-N-(3-phenoxybenzyl)-Glu(O-t-Bu)-NHCH₂CH₂OCH₂]₂

A solution of 661 mg (0.54 mmol) of crude [N-(3-nitrobenzyl)-N-(3-phenoxybenzyl)-Glu(O-t-Bu)-NHCH₂CH₂OCH₂]₂ and 2.71 g (12.0 mmol) of SnCl₂. 2H₂O in 20 mL of absolute EtOH was refluxed under N₂ for 30 min. The cooled solution was poured into 500 mL of 2.5% aqueous Na₂CO₃ with rapid stirring and the resulting cloudy mixture was extracted thoroughly with EtOAc. The slightly cloudy organic extracts were washed twice with brine, dried over Na₂SO₄, anc concentrated to give 604 mg of yellow oil which was purified by MPLC using 3% MeOH/CH₂Cl₂ to provide 350 mg (59%) of [N-(3-aminobenzyl)-N-(3-phenoxybenzyl)-Glu(O-t-Bu)-NHCH₂CH₂OCH₂]₂ as a pale yellow oil; ¹H NMR (CDCl₃, 300 MHz) 1.41 (s, 18H), 1.97 (m, 4H), 2.25 (m, 4H), 2.48 (m, 4H), 3.03 (dd, 2H, J=5, 8 Hz), 3.30 (m, 2H), 3.4-3.8 (complex, 24H), 6.47 (d, 2H, J=7.5 Hz), 6.65 (m, 4H), 6.85 (d, 2H, J=9.5 Hz), 6.9-7.15 (complex, 12H), 7.2-7.4 (complex, 8H); MS (ES+) m/z 1094 (MH+), 547 (base).

Example 20

[N-(3-Phenoxybenzyl)-N-(3-(pentanoylamino)benzyl)-Glu-NHCH₂CH₂OCH₂]₂ (cpd 247)

Pentanoyl chloride (16 uL, 16 mg, 0.136 mmol) was added dropwise to a solution of 68 mg (0.062 mmol) of

[N-(3-aminobenzyl)-N-(3-phenoxybenzyl)-Glu(O-t-Bu)-NHCH$_2$CH$_2$OCH$_2$]$_2$, 20 µL (20 mg, 0.25 mmol) of pyridine in 0.3 mL of 1,2-dichloroethane. The mixture was shaken under N$_2$ overnight and was then partitioned between EtOAc and water. The organic layer was washed with saturated aqueous NaHCO$_3$, dried over Na$_2$SO$_4$, and concentrated to give 77 mg of [N-(3-phenoxybenzyl)-N-(3-(pentanoylamino)benzyl)-Glu(O-t-Bu)-NHCH$_2$CH$_2$OCH$_2$]$_2$; MS (ES+) m/z 1073, 575 (base, MH+/2). The crude product was dissolved in 1 mL of 50% TFA/CH$_2$Cl$_2$ and allows to stand overnight. The solution was concentrated and the resulting oil was dissolved in HOAc and freeze-dried to provide 82 mg of cpd 247; $^1$H NMR (CD$_3$OD, 300 MHz) 3.98 (t, 6H, J=7.5 Hz), 1.39 (sextet, 4H, J=7.5 Hz), 1.66 (quintet, 4H, J=7.5 Hz), 1.65 (m, 2H), 1.78 (m, 2H), 2.35 (t, 4H, J=7.5 Hz), 2.45 (m, 4H), 3.38 (m, 4H), 3.50 (t, 2H, J=5), 3.57 (m, 4H), 4.10 (broad s, 8H), 6.9-7.25 (complex, 14H), 7.25-7.4 (complex, 10H), 7.71 (s, 2H); MS (ES+) m/z 1150 (MH+), 575 (base).

Example 21

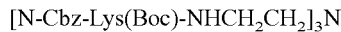

A solution of 1.0 g (2.63 mmol) of N-Cbz-Lys(Boc)OH, 0.131 mL (0.128 g, 0.876 mmol) of tris(2-aminoethyl)amine, 0.391 g (2.98 mmol) of HOBt, 0.555 g (2.89 mmol) of EDCI, and 0.55 mL (0.408 g, 3.16 mmol) of DIEA in 5 mL of CH$_2$Cl$_2$ was stirred under N$_2$ at room temperature overnight. The mixture was diluted with EtOAc and washed with 10% aqueous citric acid, saturated aqueous NaHCO$_3$, and brine. The solution was dried over Na$_2$SO$_4$ and concentrated to give 0.872 g of [N-Cbz-Lys(Boc)-NHCH$_2$CH$_2$]$_3$N as an off-white solid; $^1$H NMR (CD$_3$OD, 300 MHz) 135 (m, 12H), 1.40 (s, 27H), 1.60 (m, 3H), 1.72 (m, 3H), 2.51 (m, 6H), 2.99 (m, 6H), 3.10 (m, 3H), 3.21 (m, 3H), 4.12 (m, 3H), 5.00 (d, 3H, J=12.5 Hz), 5.08 (d, 3H, J=12.5 Hz), 7.29 (m, 15H); MS (ES+) m/z 1243 (base, MH+), 567, 467.

Example 22

A solution of 0.841 g (0.682 mmol) [N-Cbz-Lys(Boc)-NHCH$_2$CH$_2$]$_3$N, 0.252 g of 10% Pd—C, and 0.774 g (12.3 mmol) of ammonium formate in 10 mL of MeOH was stirred for 5 h at room temperature under N$_2$. The mixture was filtered through a Celite pad, the solids were washed with CH$_2$Cl$_2$, and the reslulting solution was concentrated to dryness. The residue was partitioned between CH$_2$Cl$_2$ and brine; the organic layer was dried over Na$_2$SO$_4$ and concentrated to provide 0.191 g of [Lys(Boc)-NHCH$_2$CH$_2$]$_3$N as an off-white solid; $^1$H NMR (CD$_3$OD, 300 MHz) 1.40 (s, 27H), 1.45 (m, 12H), 1.75 (m, 6H), 2.62 (m, 6H), 3.01 (m, 6H), 3.28 (m, 6H), 3.64 (m, 3H); MS (ES+) m/z 853 (MNa+), 831 (MH+), 266 (base).

Example 23

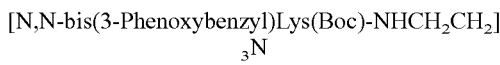

A solution of 65 mg (0.078 mmol) of [Lys(Boc)-NHCH$_2$CH$_2$]$_3$N, 120 µL (140 mg, 0.70 mmol) of 3-phenoxybenzaldehyde, and 71 µL (65 mg, 0.70 mmol) of borane-pyridine complex in 3 mL of absolute EtOH was stirred for 4 days at room temperature under N$_2$. The mixture was concentrated to dryness and partitioned between water and CH$_2$Cl$_2$. The organic layer was concentrated to give a yellow oil which was purified by MPLC using 2.5% MeOH/CH$_2$Cl$_2$ to give 78 mg of [N,N-bis(3-phenoxybenzyl)Lys (Boc)-NHCH$_2$CH$_2$]$_3$N as a yellow oil; MS (ES+) m/z 872 (base, [M—C$_{13}$H$_{12}$O)/2]+), 611, 443.

Example 24

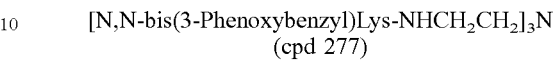

A solution of 78 mg (0.048 mmol) of [N,N-bis(3-phenoxybenzyl)Lys(Boc)-NHCH$_2$CH$_2$]$_3$N in 2 mL of 50% TFA/CH$_2$Cl$_2$ was stirred for 2 h at room temperature. The mixture was diluted with CH$_2$Cl$_2$, washed with water and 5% Na$_2$CO$_3$, and concentrated to give 57 mg of cpd 277 as an off-white foam; $^1$H NMR (CD$_3$OD, 300 MHz) 1.35 (m, 6H), 1.52 (m, 6H), 1.76 (m, 6H), 2.75 (m, 6H), 3.19 (m, 6H), 3.40 (m, 6H), 3.60 (m, 9H), 3.77 (m, 6H), 6.79 (d, 6H, J=8 Hz), 693 (m, 24H), 7.05 (m, 6H), 7.19 (m, 6H), 7.29 (m, 12H); MS (ES+) m/z 813 ([MH$_2$/2]+), 721, 542 (base, [MH/3]+).

Example 25

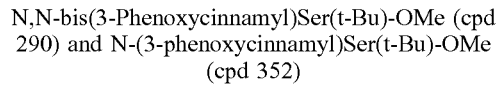

A solution of 423 mg (2.0 mmol) of H-Ser(t-Bu)OMe.HCl, 1.01 g (3.5 mmol) of 3-phenoxycinnamyl bromide (Jackson, W. P.; Islip, P. J.; Kneen, G.; Pugh, A.; Wates, P. J. *J.Med.Chem.* 31 1988; 499-500), and 0.87 mL (5.0 mmol, 650 mg) of DIEA in 6 mL of DMF was stirred under N$_2$ at room temperature for 20 h. The mixture was partitioned between EtOAc and water and the organic layer was washed with water and brine. After drying over Na$_2$SO$_4$, the organic solution was concentrated to give 0.98 g of yellow oil. The crude residue was purified by MPLC using a solvent gradient ranging from 10-30% EtOAc/hexanes to give two products. The less polar product (168 mg, 14% based on starting amino acid), N,N-bis(3-phenoxycinnamyl)Ser(t-Bu)-OMe (cpd 290), was isolated as a pale yellow oil; $^1$H NMR (CDCl$_3$, 300 MHz) 1.15 (s, 9H), 3.35 (dd, 2H, J=7, 14.5 Hz), 3.53 (dd, 2H, J=5.5, 14.5 Hz), 3.6-3.8 (complex, 3H), 3.69 (s, 3H), 6.18 (dt, 2H, J=16, 6.5 Hz), 6.49 (d, 2H, J=16 Hz), 6.86 (dd, 2H, J=2, 8 Hz), 6.9-7.4 (complex, 16H); MS (ES+) m/z 614, 592 (MH+, base), 406, 384, 209.

The more polar product (354 mg, 46% based on starting amino acid), N-(3-phenoxycinnamyl)Ser(t-Bu)-OMe (cpd 352), was isolated as a pale yellow oil; $^1$H NMR (CDCl$_3$, 300 MHz) 1.15 (s, 9H), 1.98 (broad s, 1H), 3.32 (ddd, 1H, J=1.2, 6.5, 14 Hz), 3.4-3.7 (complex, 4H), 3.72 (s, 3H), 6.21 (dt, 1H, J=16, 6.5 Hz), 6.48 (d, 1H, J=16 Hz), 6.88 (dd, 1H, J=1.5, 8 Hz), 7.0-7.4 (complex, 8H); MS (ES+) m/z 789 (2M+Na+), 384 (MH+, base), 209.

Example 26

N,N-Bis(3-phenoxycinnamyl)Ser(t-Bu)-OMe (cpd 290, 168 mg, 0.284 mmol) was stirred in 3 mL of 50% TFA/CH$_2$Cl$_2$ under N$_2$ overnight. The solvent was removed using a rotary evaporator and the crude residue was partitioned between EtOAc and saturated aqueous NaHCO$_3$. After washing with brine and drying over Na₂SO₄, the organic layer was concentrated using a rotary evaporator and the crude product (134 mg) was purified by MPLC using 30% EtOAc/hexanes to give 44 mg (29%) of N,N-bis(3-phenoxycinnamyl)Ser-OMe (cpd 299) as a colorless oil; ¹H NMR (CDCl₃, 300 MHz) 1.6 (broad s, 2H), 3.38 (dd, 2H, J=8, 12 Hz), 3.4-3.9 (complex, 5H), 3.72 (s, 3H), 6.13 (dt, 2H, J=16, 7 Hz), 6.50 (d, 2H, J=16 Hz), 6.8-7.4 (complex, 18H); MS (ES+) m/z 536 (MH+).

Example 27

N,N-Bis(3-phenoxycinnamyl)Ser-OH (cpd 300)

N,N-Bis(3-phenoxycinnamyl)Ser-OMe (cpd 299, 44 mg, 0.082 mmol) was dissolved in 0.2 mL of MeOH and was stirred with 0.090 mL of 1N aqueous NaOH. When TLC analysis revealed that starting material had been consumed, the solvent was removed by rotary evaporation and the residue was lyophilized from acetic acid to give 42 mg (88%) of N,N-bis(3-phenoxycinnamyl)Ser-OH acetate (cpd 300) as a sticky yellow solid; ¹H NMR (methanol-d₄, 300 M) 1.97 (s, 3H), 3.3-4.2 (complex, 7H), 6.80 (d, 2H, J=16 Hz), 6.9-7.4 (complex, 18H); MS (ES+) m/z 522 (MH+), 209.

Example 28

N-(3-Phenoxycinnamyl)Ser-OMe (cpd 346)

N-(3-Phenoxycinnamyl)Ser(t-Bu)-OMe (cpd 352, 268 mg, 0.699 mmol) was stirred in 3 mL of 50% TFA/CH₂Cl₂ under N₂ overnight. The solvent was removed using a rotary evaporator and the crude residue (256 mg) was purified by MPLC using EtOAc to give 137 mg (60%) of N-(3-phenoxycinnamyl)Ser-OMe (cpd 346) as a colorless oil; ¹H NMR (CDCl₃, 300 MHz) 2.2 (broad s, 2H), 3.36 (dd, 1H, J=6, 14 Hz), 3.4-3.5 (complex, 2H), 3.62 (dd, 1H, J=6.5, 11 Hz), 3.74 (s, 3H), 3.80 (dd, 1H, J=4.5, 11 Hz). 6.19 (dt, 1H, J=16, 6.5 Hz), 6.48 (d, 1H, J=6 Hz), 6.88 (dd, 1H, J=1.5, 8 Hz), 7.0-7.4 (complex, 8H); MS (ES+) m/z 677 (2M+Na+), 350 (M+Na+), 328 (MH+), 209 (base).

Example 29

N-(3-phenoxycinnamyl)Ser-OH (cpd 347)

N-(3-Phenoxycinnamyl)Ser-OMe (cpd 346, 110 mg, 0.336 mmol) was dissolved in 1.5 mL of MeOH and was stirred with 0.50 mL of 1N aqueous NaOH. When TLC analysis revealed that starting material had been consumed, the solvent was removed by rotary evaporation. The residue was dissolved in water and acidified to pH 7-8 with 1N aqueous HCl; the resulting solids were filtered, washed with water, and dried to give 71 mg of white powder. The insoluble powder was dissolved in TFA and, after removal of excess TFA by rotary evaporation, lyophilized from acetic acid to give 82 mg (57%) of N-(3-phenoxycinnamyl)Ser-OH trifluoroacetate (cpd 347) as an amber oil; ¹H NMR (methanol-d₄, 300 MHz) 3.88 (d, 2H, J=7H), 4.0-4.2 (complex, 3H), 6.27 (dt, 1H, J=16, 6.5), 6.83 (d, 1H, J=16 Hz), 6.9-7.4 (complex, 9H); MS (ES+) m/z 314, (MH+), 209.

Example 30

N-(3-Phenoxycinnamyl)Glu(O-t-Bu)-OH (cpd 337)

A mixture of 249 mg (0.585 mmol) of N-(3-phenoxycinnamyl)Glu(O-t-Bu)-OMe (cpd 334) in 3 mL of MeOH was sonicated to speed dissolution, and the resulting solution was treated with 0.585 mL of 1N aqueous NaOH. After stirring overnight, the MeOH was removed using a rotary evaporator and the residue was dissolved in water. Acidification with 0.64 mL of 1N aqueous HCl produced a 250 mg of solid material that was triturated with Et₂O to give 111 mg (46%) of N-(3-phenoxycinnamyl)Glu(O-t-Bu)-OH (cpd 337) as a white solid; ¹H NMR (300 MHz, methanol-d₄) 1.43 (s, 9H), 1.9-2.2 (complex, 2H), 2.46 (t, 2H, J=7 Hz), 3.57 (dd, 1H, J=5, 7 Hz), 3.78 (dd, 1H, J=7, 13.5 Hz), 3.82 (dd, 1H, J=7, 13.5 Hz), 6.28 (dt, 1H, J=16, 7 Hz), 6.81 (d, 1H, J=16 Hz), 6.9-7.5 (complex, 9H); MS (ES+) m/z 412 (MH+, base), 356, 209. Anal. Calcd for C₂₄H₂₉NO₅.0.4 H₂O: C, 68.55; H, 7.04; N, 3.24. Found: C, 68.89; H, 7.04; N, 3.24.

Example 31

N-(3-Phenoxycinnamyl)Glu-OH (cpd 326)

A mixture of 85 mg (0.21 mmol) of N-(3-phenoxycinnamyl)Glu(O-t-Bu)-OH (cpd 337) in was stirred in 1 mL of 50% TFA/CH₂Cl₂ for 1 h. After solvent removal using a rotary evaporator, the residue was dissolved in acetic acid and freeze-dried to give 75 mg (76%) of N-(3-phenoxycinnamyl)Glu-OH tifluoroacetate (cpd 326) as a fluffy white solid; ¹H NMR (300 MHz, methanol-₄) 2.0-2.4 (complex, 2H), 2.55 (m, 2H), 3.84 (d, 2H, J=7 Hz), 3.96 (dd, 1H, J=5, 7 Hz, 6.24 (dt, 1H, J=16, 7 Hz), 6.84 (d, 1H, J=16 Hz), 6.9-7.4 (complex, 9H); MS (ES+) m/z 356 (MH+), 209 (base).

TABLE 2

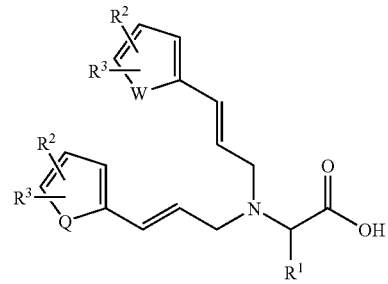

| cpd | % inh | R¹ (amino acid side chain) | R² | R³ | W, Q |
|---|---|---|---|---|---|
| 11 | 70 | Asn, Asp, Gln, Glu | 3-PhO | | CH=CH |
| 12 | 59 | Cys, Met, Ser, Thr | 3-PhO | | CH=CH |
| 13 | nd | Arg, Gly, His, Pro | 3-PhO | | CH=CH |
| 14 | 30 | Lys(2-Cl—Cbz), Phe, Trp, Tyr | 3-PhO | | CH=CH |
| 15 | 48 | Ala, Ile, Leu, Val | 3-PhO | | CH=CH |
| 16 | nd | Glu, Asp | 2,3-benzo | | CH=CH |
| 17 | nd | Cys, Met | 2,3-benzo | | CH=CH |
| 18 | nd | Ser, Thr | 2,3-benzo | | CH=CH |
| 19 | nd | His, Arg(Mtr) | 2,3-benzo | | CH=CH |
| 20 | nd | Pro, Gly | 2,3-benzo | | CH=CH |
| 21 | nd | Phe, Tyr | 2,3-benzo | | CH=CH |
| 22 | nd | Trp, Lys(2-Cl—Cbz) | 2,3-benzo | | CH=CH |
| 23 | nd | Ile, Ala | 2,3-benzo | | CH=CH |
| 24 | nd | Val, Leu | 2,3-benzo | | CH=CH |
| 25 | nd | Asn, Lys | 2,3-benzo | | CH=CH |
| 26 | nd | Ala, Ile | | 3,4-benzo | CH=CH |
| 27 | nd | Arg(Mtr), Lys(2-Cl—Cbz) | | 3,4-benzo | CH=CH |
| 28 | nd | Asp, Glu | | 3,4-benzo | CH=CH |
| 29 | nd | Cys, Met | | 3,4-benzo | CH=CH |
| 30 | nd | Gly, Pro | | 3,4-benzo | CH=CH |
| 31 | nd | His, Lys | | 3,4-benzo | CH=CH |

TABLE 2-continued

| cpd | % inh | R¹ (amino acid side chain) | R² | R³ | W, Q |
|---|---|---|---|---|---|
| 32 | nd | Leu, Val | | 3,4-benzo | CH=CH |
| 33 | nd | Lys(2-Cl—Cbz), Phe | | 3,4-benzo | CH=CH |
| 34 | nd | Ser, Thr | | 3,4-benzo | CH=CH |
| 35 | nd | Trp, Tyr | | 3,4-benzo | CH=CH |

TABLE 3

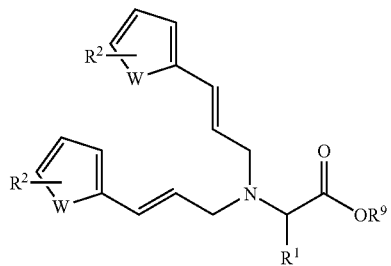

| cpd | EPO/EBP-Ig % inh @ 50 μM | R¹ | R² | R⁹ | W, Q | MS MH+ |
|---|---|---|---|---|---|---|
| 36 | nd | $CH_3$ | 4-$CF_3$ | H | CH=CH | 458 |
| 37 | 19 | H | 4-$CF_3$ | H | CH=CH | 430 |
| 38 | nd | $(CH_2)_4NH(2\text{-}Cl\text{—}Cbz)$ | 4-F | H | CH=CH | 448 |
| 40 | nd | $CH_3$ | 4-F | H | CH=CH | 223 |
| 41 | nd | $CH_2CO_2H$ | 4-F | H | CH=CH | 266 |
| 42 | nd | $CH_2CH_2CO_2H$ | 4-F | H | CH=CH | 281 |
| 43 | nd | $(CH_2)_3NHC(=NH)NH_2$ | 4-F | H | CH=CH | 308 |
| 45 | nd | $PhCH_2$ | 4-F | H | CH=CH | 299 |
| 46 | nd | 4-HO—$PhCH_2$ | 4-F | H | CH=CH | 315 |
| 47 | nd | $CH_2OH$ | 4-F | H | CH=CH | 238 |
| 48 | nd | $CH(OH)CH_3$ | 4-F | H | CH=CH | 253 |
| 49 | 1 | $(CH_2)_3NHC(=NH)NH_2$ | H | H | S | 419 |
| 50 | −6 | $(CH_2)_4NH_2$ | H | H | S | 391 |
| 51 | nd | $CH(CH_3)CH_2CH_3$ | H | H | S | 376 |
| 52 | 21 | $CH_2CH_2CO_2H$ | H | H | S | 392 |
| 53 | 14 | $CH_2CO_2H$ | H | H | S | 378 |
| 54 | 18 | $CH_3$ | H | H | S | 334 |
| 55 | 4 | $CH_2CH_2CONH_2$ | H | H | S | 391 |
| 56 | nd | $(CH_2)_4NHCbz$ | H | Me | S | 539 |
| 57 | 0 | $(CH_2)_4NHCbz$ | H | $CH_2Ph$ | S | 615 |
| 58 | nd | $CH_2(\text{indol-3-yl})$ | H | Me | S | 463 |
| 59 | 26 | $CH_2CH_2CO_2\text{-}t\text{-}Bu$ | H | Me | S | 462 |
| 60 | 9 | $CH_2CH_2CO_2Et$ | H | Me | S | 434 |
| 61 | 14 | $CH_2CH_2CO_2H$ | H | Me | S | 406 |

TABLE 4

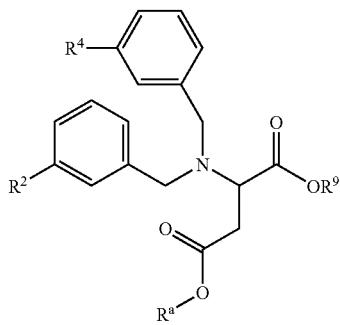

| cpd | EPO/EBP-Ig % inh @ 50 μM | $R^a$ | $R^2$ | $R^4$ | $R^9$ | MS, MH+ |
|---|---|---|---|---|---|---|
| 62 | nd | t-Bu | $NO_2$ | $NO_2$ | t-Bu | 516 |
| 63 | 20 | H | $PhCH_2NH$ | PhO | H | 511 |
| 64 | −4 | H | 4-MePhCONH | 4-MePhCONH | H | 580 |
| 65 | −7 | H | 4-MePhSO$_2$NH | 4-MePhSO$_2$NH | H | 652 |
| 66 | −16 | H | 3-ClPhCH$_2$NH | PhO | H | 546 |
| 67 | −8 | H | 3-BrPhCH$_2$NH | PhO | H | 590 |
| 68 | −13 | H | 2-FPhCH$_2$NH | PhO | H | 529 |
| 69 | −13 | H | 2-MePhCH$_2$NH | PhO | H | 525 |
| 70 | −8 | H | 4-FPhCH$_2$NH | PhO | H | 529 |
| 71 | −6 | H | 3-ClPhCH$_2$NH | 4-Me—PhO | H | 560 |
| 72 | −14 | H | F$_5$—PhCH$_2$NH | 4-Me—PhO | H | 615 |
| 73 | −13 | H | 2-FPhCH$_2$NH | 4-Me—PhO | H | 543 |
| 74 | −7 | H | 3-CNPhCH$_2$NH | 4-Me—PhO | H | 550 |
| 75 | −2 | H | PhCH$_2$NH | 4-Me—PhO | H | 525 |

TABLE 5

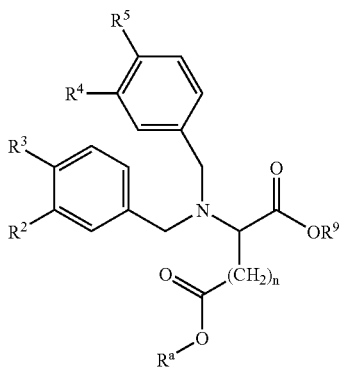

| cpd | EPO/EBP-Ig % inh @ 50 μM | $R^a$ | $R^2$ | $R^3$ | $R^4$ | $R^5$ | $R^9$ | n | MS, MH+ |
|---|---|---|---|---|---|---|---|---|---|
| 76 | 25 | t-Bu | PhO | H | PhO | H | t-Bu | 1 | 636 |
| 77 | 52 | H | PhO | H | PhO | H | H | 1 | 524 |
| 78 | nd | H | H | 4-MePhCONH | H | BnO | H | 2 | 593 |
| 79 | nd | H | H | n-BuCONH | H | BnO | H | 2 | 559 |
| 80 | nd | H | H | 2-naphthyl CONH | H | BnO | H | 2 | 629 |
| 81 | nd | H | H | 2-furyl CONH | H | BnO | H | 2 | 569 |
| 82 | 32 | H | H | 4-MeO—PhCONH | H | BnO | H | 2 | 609 |
| 83 | 18 | H | H | HO$_2$C(CH$_2$)$_3$CONH | H | BnO | H | 2 | 589 |
| 84 | 14 | H | H | C$_2$F$_5$CONH | H | BnO | H | 2 | 621 |
| 85 | 20 | H | H | CF$_3$CONH | H | BnO | H | 2 | 571 |
| 86 | 37 | H | H | 4-pyridyl-CONH | H | BnO | H | 2 | 580 |
| 87 | 23 | H | H | 4-MePhSO$_2$NH | H | BnO | H | 2 | 629 |
| 88 | 10.3 | H | H | HO$_2$CCH$_2$(1,1-cyclopentyl)CH$_2$CONH | H | BnO | H | 2 | 643 |
| 89 | 22 | H | H | PhOCONH | H | BnO | H | 2 | 595 |
| 90 | 29 | H | H | 4-Ph—PhCONH | H | BnO | H | 2 | 655 |
| 91 | 19 | H | H | 4-NO$_2$—PhCONH | H | BnO | H | 2 | 624 |

TABLE 6

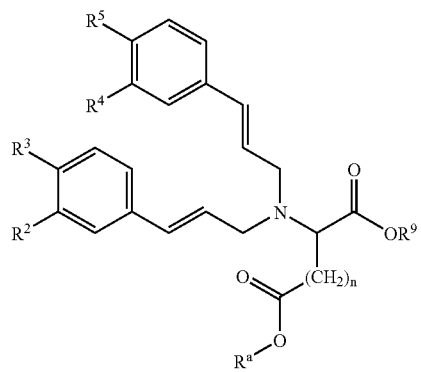

| cpd | EPO/EBP-Ig % inh @ 50 μM | $R^a$ | $R^2$ | $R^3$ | $R^4$ | $R^5$ | $R^6$ | $R^9$ | MS, MH+ |
|---|---|---|---|---|---|---|---|---|---|
| 92 | 20 | H | H | H | H | H | 2 | Me | 394 |
| 93 | 20 | t-Bu | H | H | H | H | 2 | Me | 450 |
| 94 | 25 | Et | H | H | H | H | 2 | Me | 422 |
| 95 | 15 | t-Bu | 2,3-benzo | 2,3-benzo | | | 2 | Me | 550 |
| 96 | −5 | t-Bu | PhO | H | PhO | H | 2 | Me | 634 |
| 97 | 14 | t-Bu | 3,4-benzo | 3,4-benzo | | | 2 | H | 536 |
| 98 | 12 | t-Bu | H | Ph | H | Ph | 2 | Me | 602 |
| 99 | 13 | t-Bu | 3,4-di-Cl—PhO | H | 3,4-di-Cl—PhO | H | 2 | Me | 772 |
| 100 | 34 | H | H | Ph | H | Ph | 2 | Me | 546 |
| 101 | 32 | H | 3,4-di-Cl—PhO | H | 3,4-di-Cl—PhO | H | 2 | Me | 716 |
| 102 | 5 | t-Bu | 4-t-Bu—PhO | H | 4-t-Bu—PhO | H | 2 | t-Bu | 789 |
| 103 | 17 | t-Bu | 3-CF3—PhO | H | 3-CF3—PhO | H | 2 | t-Bu | 812 |
| 104 | 78 | H | 4-t-Bu—PhO | H | 4-t-Bu—PhO | H | 2 | H | 676 |
| 105 | 70 | H | 3-CF3—PhO | H | 3-CF3—PhO | H | 2 | H | 700 |
| 106 | 20 | t-Bu | PhO | H | PhO | H | 1 | t-Bu | 662 |
| 107 | 78 | H | PhO | H | PhO | H | 2 | H | 562* |
| 108 | 81 | H | PhO | H | PhO | H | 1 | H | 550 |

*[M − H]−

TABLE 7

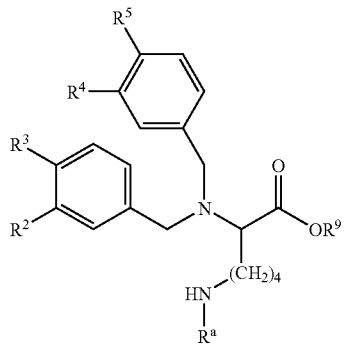

| cpd | EPO/ EBP-Ig % inh @ 50 μM | $R^a$ | $R^2$ | $R^3$ | $R^4$ | $R^5$ | $R^9$ | MS, MH+ |
|---|---|---|---|---|---|---|---|---|
| 109 | 7 | Boc | BnO | H | BnO | H | Me | 653 |
| 110 | 54 | H | H | BnO | H | BnO | Me | 553 |
| 111 | 5 | Boc | H | BnO | H | BnO | Me | 653 |
| 112 | 59 | H | BnO | H | BnO | H | Me | 553 |
| 113 | 24 | Boc | H | BnO | NO2 | H | Me | 592 |
| 114 | 37 | H | H | BnO | NO2 | H | Me | 492 |
| 115 | 35 | H | H | BnO | NH2 | H | Me | 462 |
| 116 | 32 | H | H | BnO | n-BuCONH | H | Me | 546 |
| 117 | 34 | H | H | BnO | 2-furylCONH | H | Me | 556 |
| 118 | 36 | H | H | BnO | 4-MePhCONH | H | Me | 580 |
| 119 | 34 | H | H | BnO | i-Pr—CONH | H | Me | 532 |

TABLE 7-continued

[Structure: N,N-dibenzyl amino acid ester with R²,R³ on one benzyl ring, R⁴,R⁵ on other benzyl ring, (CH₂)₄NHRᵃ side chain, CO₂R⁹]

| cpd | EPO/EBP-Ig % inh @ 50 μM | Rᵃ | R² | R³ | R⁴ | R⁵ | R⁹ | MS, MH+ |
|---|---|---|---|---|---|---|---|---|
| 120 | 35 | H | H | BnO | 4-pyridyl-CONH | H | Me | 567 |
| 121 | 45 | H | H | BnO | 2-naphthyl-CONH | H | Me | 616 |
| 122 | nd | Boc | PhCH₂NH | H | PhCH₂NH | H | Me | 651 |
| 123 | nd | Boc | 2-MePhCH₂NH | H | 2-MePhCH₂NH | H | Me | 679 |
| 124 | nd | Boc | 4-MeO—PhCH₂NH | H | 4-MeO—PhCH₂NH | H | Me | 711 |
| 125 | nd | Boc | 3,4-di-MeO—PhCH₂NH | H | 3,4-di-MeO—PhCH₂NH | H | Me | 771 |
| 126 | nd | Boc | —NH₂ | H | —NH₂ | H | Me | 417 |
| 127 | nd | H | PhCH₂NH | H | PhCH₂NH | H | Me | 551 |
| 128 | nd | H | 2-MePhCH₂NH | H | 2-MePhCH₂NH | H | Me | 579 |
| 129 | nd | H | 4-MeO—PhCH₂NH | H | 4-MeO—PhCH₂NH | H | Me | 611 |
| 130 | nd | H | 3,4-di-MeO—PhCH₂NH | H | 3,4-di-MeO—PhCH₂NH | H | Me | 671 |
| 131 | nd | H | PhCH₂CH₂NH | H | PhCH₂CH₂NH | H | Me | 579 |
| 132 | nd | HO₂CCH₂CH₂CO | PhCH₂NH | H | PhCH₂NH | H | Me | 651 |
| 133 | nd | HO₂CCH₂CH₂CO | 2-MePhCH₂NH | H | 2-MePhCH₂NH | H | Me | 679 |
| 134 | nd | HO₂CCH₂CH₂CO | 4-MeO—PhCH₂NH | H | 4-MeO—PhCH₂NH | H | Me | 711 |
| 135 | nd | HO₂CCH₂CH₂CO | 3,4-di-MeO—PhCH₂NH | H | 3,4-di-MeO—PhCH₂NH | H | Me | 771 |
| 136 | nd | HO₂CCH₂CH₂CO | PhCH₂CH₂NH | H | PhCH₂CH₂NH | H | Me | 679 |

TABLE 8

[Structure: N-cinnamyl-N-benzyl amino acid ester with R² on cinnamyl phenyl, R⁴,R⁵ on benzyl ring, (CH₂)₄NHRᵃ side chain, CO₂R⁹]

| cpd | EPO/EBP-Ig % inh @ 50 μM | Rᵃ | R² | R⁴ | R⁵ | R⁹ | MS, MH+ |
|---|---|---|---|---|---|---|---|
| 137 | nd | H | PhO | PhO | H | Me | 551 |
| 138 | nd | Boc | 4-t-Bu—PhO | BnO | H | Me | 721 |

TABLE 8-continued

| cpd | EPO/EBP-Ig % inh @ 50 μM | R$^a$ | R$^2$ | R$^4$ | R$^5$ | R$^9$ | MS, MH+ |
|---|---|---|---|---|---|---|---|
| 139 | nd | H | 4-t-Bu—PhO | BnO | H | Me | 621 |
| 140 | nd | H | (CF$_3$CO)$_2$N | BnO | H | H | 666 |
| 141 | nd | H | PhCONH | BnO | H | H | 578 |
| 142 | nd | H | 4-pyridyl-CONH | BnO | H | H | 579 |
| 143 | nd | H | (CF$_3$CO)$_2$N | PhO | H | H | 652 |
| 144 | nd | H | PhCONH | PhO | H | H | 564 |
| 145 | nd | H | 4-pyridyl-CONH | PhO | H | H | 565 |
| 146 | nd | H | (CF$_3$CO)$_2$N | MeO | MeO | H | 620 |
| 147 | nd | H | PhCONH | MeO | MeO | H | 532 |
| 148 | nd | H | 4-pyridyl-CONH | MeO | MeO | H | 533 |
| 149 | nd | H | (CF$_3$CO)$_2$N | H | PhO | H | 652 |
| 150 | nd | H | PhCONH | H | PhO | H | 564 |
| 151 | nd | H | 4-pyridyl-CONH | H | PhO | H | 565 |
| 152 | nd | H | PhCONH | H | BnO | H | 578 |
| 153 | nd | H | 4-pyridyl-CONH | H | BnO | H | 579 |
| 154 | nd | H | (CF$_3$CO)$_2$N | H | BnO | H | 666 |
| 155 | nd | HO$_2$CCH$_2$CH$_2$CO | 4-MeO—PhCONH | PhO | H | H | 694 |
| 156 | nd | HO$_2$CCH$_2$CH$_2$CO | PhCONH | PhO | H | H | 664 |
| 157 | nd | HO$_2$CCH$_2$CH$_2$CO | 2-naphthyl-CONH | PhO | H | H | 714 |
| 158 | nd | HO$_2$CCH$_2$CH$_2$CO | 4-Me—PhSO$_2$NH | PhO | H | H | 714 |
| 159 | nd | HO$_2$CCH$_2$CH$_2$CO | 4-MeO—PhCONH | 2,3-benzo | | H | 652 |
| 160 | nd | HO$_2$CCH$_2$CH$_2$CO | PhCONH | 2,3-benzo | | H | 622 |
| 161 | nd | HO$_2$CCH$_2$CH$_2$CO | 2-naphthyl-CONH | 2,3-benzo | | H | 672 |
| 162 | nd | HO$_2$CCH$_2$CH$_2$CO | 4-Me—PhSO$_2$NH | 2,3-benzo | | H | 672 |
| 163 | nd | HO$_2$CCH$_2$CH$_2$CO | 4-MeO—PhCONH | H | F | H | 620 |
| 164 | nd | HO$_2$CCH$_2$CH$_2$CO | PhCONH | H | F | H | 590 |
| 165 | nd | HO$_2$CCH$_2$CH$_2$CO | 2-naphthyl-CONH | H | F | H | 640 |
| 166 | nd | HO$_2$CCH$_2$CH$_2$CO | 4-Me—PhSO$_2$NH | H | F | H | 640 |
| 167 | nd | HO$_2$CCH$_2$CH$_2$CO | 4-MeO—PhCONH | BnO | H | H | 708 |
| 168 | nd | HO$_2$CCH$_2$CH$_2$CO | PhCONH | BnO | H | H | 678 |
| 169 | nd | HO$_2$CCH$_2$CH$_2$CO | 2-naphthyl-CONH | BnO | H | H | 728 |
| 170 | nd | HO$_2$CCH$_2$CH$_2$CO | 4-Me—PhSO$_2$NH | BnO | H | H | 728 |

TABLE 9

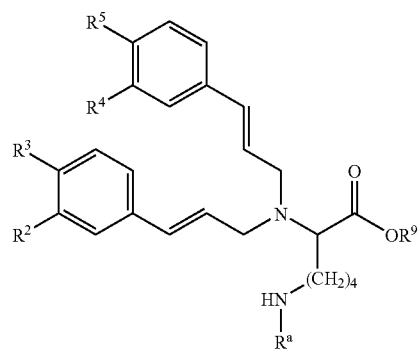

| cpd | EPO/EBP-Ig % inh @ 50 μM | $R^a$ | $R^2$ | $R^3$ | $R^4$ | $R^5$ | $R^9$ | MS, MH+ |
|---|---|---|---|---|---|---|---|---|
| 171 | nb | Cbz | H | H | H | H | Me | 527 |
| 172 | 15 | Cbz | H | H | H | H | H | 513 |
| 173 | 5 | Cbz | H | H | H | H | t-Bu | 569 |
| 174 | 23 | Cbz | H | MeO | H | MeO | Me | 587 |
| 175 | 1 | Cbz | | 3,4-benzo | | 3,4-benzo | Me | 627 |
| 176 | −4 | Cbz | PhO | H | PhO | H | Me | 711 |
| 177 | nd | Cbz | 2,3-benzo | | 2,3-benzo | | Me | 627 |
| 178 | 36 | Boc | H | $NO_2$ | H | $NO_2$ | Me | 583 |
| 179 | 30 | Boc | H | $NO_2$ | H | $NO_2$ | H | 569 |
| 180 | −4 | Boc | PhO | H | PhO | H | Me | 677 |
| 181 | −9 | Boc | 4-t-Bu—PhO | H | 4-t-Bu—PhO | H | Me | 790 |
| 182 | 18 | H | 4-t-Bu—PhO | H | 4-t-Bu—PhO | H | Me | 689 |
| 183 | 36 | Boc | $NO_2$ | H | $NO_2$ | H | Me | 583 |
| 184 | 53 | H | $NO_2$ | H | $NO_2$ | H | Me | 483 |
| 185 | 29 | H | $NH_2$ | H | $NH_2$ | H | Me | 423 |
| 186 | nd | H | n-Bu—CONH | H | n-Bu—CONH | H | Me | 591 |
| 187 | nd | H | 2-furyl-CONH | H | 2-furyl-CONH | H | Me | 611 |
| 188 | nd | H | PhCONH | H | PhCONH | H | Me | 631 |
| 189 | nd | H | 4-Me—PhCONH | H | 4-Me—PhCONH | H | Me | 659 |
| 190 | nd | H | 4-$NO_2$—PHCONH | H | 4-$NO_2$—PHCONH | H | Me | 721 |
| 191 | nd | H | 4-Me—PH$SO_2$NH | H | 4-Me—PH$SO_2$NH | H | Me | 731 |
| 192 | nd | H | Cbz—NH | H | Cbz—NH | H | Me | 691 |
| 193 | nd | H | 4-Br—PhCONH | H | 4-Br—PhCO | H | Me | 789 |
| 194 | nd | H | 2-MeO—PhCONH | H | 2-MeO—PhCONH | H | Me | 691 |
| 195 | nd | H | 3-MeO—PhCONH | H | 3-MeO—PhCONH | H | Me | 691 |
| 196 | nd | H | 4-MeO—PhCONH | H | 4-MeO—PhCONH | H | Me | 691 |
| 197 | nd | H | $CH_3$CH=CHCONH | H | $CH_3$CH=CHCONH | H | Me | 559 |
| 198 | nd | H | $C_2F_5$CONH | H | $C_2F_5$CONH | H | Me | 715 |
| 199 | nd | H | 2-naphthyl-CONH | H | 2-naphthyl-CONH | H | Me | 731 |
| 200 | nd | H | $EtO_2$C$CH_2CH_2$CONH | H | $EtO_2$C$CH_2CH_2$CONH | H | Me | 679 |
| 201 | nd | H | $CF_3$CONH | H | $CF_3$CONH | H | Me | 615 |
| 202 | nd | H | $MeSO_2$NH | H | $MeSO_2$NH | H | Me | 579 |

TABLE 10

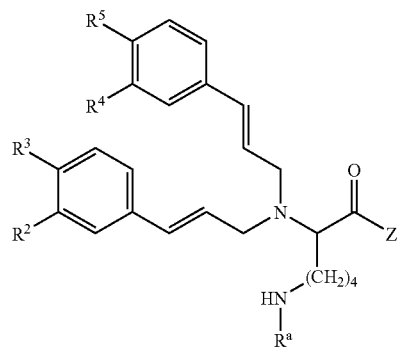

| cpd | EPO/EBP-Ig % inh @ 50 μM | $R^a$ | $R^2$ | $R^3$ | $R^4$ | $R^5$ | Z | MS, MH+ |
|---|---|---|---|---|---|---|---|---|
| 203 | 37 | Boc | H | H | H | H | 4-(MeCOCH$_2$CH$_2$)—PhNH | 640 |
| 204 | −6 | H | H | H | H | H | 4-(MeCOCH$_2$CH$_2$)—PhNH | 540 |
| 205 | 26 | H | H | H | H | H | n-Bu-NH | 434 |
| 206 | 17 | 2-MeO—PhCO | H | H | H | H | n-Bu—NH | 568 |
| 207 | 20 | 4-MeO—PhCO | H | H | H | H | n-Bu—NH | 568 |
| 208 | 22 | PhCO | H | H | H | H | n-Bu—NH | 538 |
| 209 | 25 | 2-MeO—PhCO | H | H | H | H | n-Bu—NH | 568 |
| 210 | nd | Boc | H | H | H | H | 4-MeO—PhCH$_2$CH$_2$NH | 612 |
| 211 | 62 | H | H | H | H | H | 4-MeO—PhCH$_2$CH$_2$NH | 512 |
| 212 | −10 | H | H | H | H | H | n-Pr—NH | 420 |
| 214 | nd | Boc | H | H | H | H | 3,4-di-MeO—PhCH$_2$CH$_2$NH | 642 |
| 215 | nd | Boc | H | H | H | H | 3-MeO—PhCH$_2$CH$_2$NH | 612 |
| 216 | 10 | Boc | H | H | H | H | 4-(PhCH=CHCH$_2$O)—PhCH$_2$NH | 700 |
| 217 | nd | Boc | H | H | H | H | 4-HO—PhCH$_2$NH | 584 |
| 218 | nd | Boc | H | H | H | H | EtNH | 506 |
| 219 | nd | Boc | H | H | H | H | MeNH | 492 |
| 220 | 45 | H | H | H | H | H | 4-(PhCH=CHCH$_2$O)—PhCH$_2$NH | 600 |
| 221 | 48 | H | H | H | H | H | 3,4-di-MeO—PhCH$_2$CH$_2$NH | 542 |
| 222 | 56 | H | H | H | H | H | 3-MeO—PhCH$_2$CH$_2$NH | 512 |
| 223 | nd | Boc | H | H | H | H | 2-MeO—PhCH$_2$CH$_2$NH | 612 |
| 224 | 51 | H | H | H | H | H | 2-MeO—PhCH$_2$CH$_2$NH | 512 |
| 225 | 10 | Boc | PhO | H | PhO | H | 4-MeO—PhCH$_2$CH$_2$NH | 797 |
| 226 | nd | Boc | H | H | H | H | PhCH$_2$CH$_2$NH | 582 |
| 227 | 48 | H | H | H | H | H | PhCH$_2$CH$_2$NH | 482 |
| 228 | 21 | PhNHCO | PhO | H | PhO | H | 4-MeO—PhCH$_2$CH$_2$NH | 816 |
| 229 | 22 | 4-PhO—PhNHCO | H | H | H | H | 4-MeO—PhCH$_2$CH$_2$NH | 723 |
| 230 | 42 | 3,4-di-Cl—PhNHCO | H | H | H | H | 4-MeO—PhCH$_2$CH$_2$NH | 700 |
| 231 | 36 | 4-EtO2C—PhNHCO | H | H | H | H | 4-MeO—PhCH$_2$CH$_2$NH | 703 |
| 232 | 14 | 4-PhO—PhNHCO | PhO | H | PhO | H | 4-MeO—PhCH$_2$CH$_2$NH | 908 |
| 233 | 18 | H | H | NO2 | H | NO2 | 4-MeO—PhCH$_2$CH$_2$NH | 602 |
| 234 | nd | Boc | H | H | H | H | PhCH$_2$NH | 568 |
| 235 | 49 | H | H | H | H | H | PhCH$_2$NH | 468 |
| 236 | nd | Boc | H | Ph | H | Ph | 4-MeO—PhCH$_2$CH$_2$NH | 765 |
| 237 | 55 | HO$_2$CCH$_2$CH$_2$CO | H | H | H | H | 3-MeO—PhCH$_2$CH$_2$NH | 612 |
| 238 | 39 | H | H | Ph | H | Ph | 4-MeO—PhCH$_2$CH$_2$NH | 664 |
| 239 | 46 | H | PhO | H | PhO | H | PhCH$_2$CH$_2$NH | 666 |
| 240 | nd | HO$_2$CCH$_2$CH$_2$CH$_2$CO | PhO | H | PhO | H | PhCH$_2$CH$_2$NH | 780 |
| 285 | 40 | H | H | H | H | H | 4-(NH$_2$CO)piperidin-1-yl | 489 |

TABLE 11

[Structure: dibenzyl-N with ester and amide substituents, bracketed ×2]

| cpd | EPO/EBP-Ig % inh @ 50 μM | R$^a$ | R$^2$ | R$^3$ | R$^4$ | R$^5$ | Z | r | MS, [MH$_2$/2]+ |
| --- | --- | --- | --- | --- | --- | --- | --- | --- | --- |
| 241 | 2 | t-Bu | H | BnO | H | BnO | NH(CH$_2$)$_3$O(CH$_2$)$_4$O(CH$_2$)$_3$NH | 1 | 666 |
| 242 | 1 | t-Bu | H | BnO | H | BnO | NH(CH$_2$)$_3$O(CH$_2$CH$_2$O)$_2$(CH$_2$)$_3$NH | 1 | 674 |
| 243 | 75 | H | H | BnO | H | BnO | NH(CH$_2$)$_3$O(CH$_2$)$_4$O(CH$_2$)$_3$NH | 1 | 610 |
| 244 | 66 | H | H | BnO | H | BnO | NH(CH$_2$)$_3$O(CH$_2$CH$_2$O)$_2$(CH$_2$)$_3$NH | 1 | 618 |
| 245 | 0 | t-Bu | H | BnO | H | BnO | NH(CH$_2$)$_2$O(CH$_2$)$_2$O(CH$_2$)$_2$NH | 2 | 652 |
| 246 | 79 | H | H | BnO | H | BnO | NH(CH$_2$)$_2$O(CH$_2$)$_2$O(CH$_2$)$_2$NH | 2 | 596 |
| 247 | 47 | H | n-Bu—CONH | H | PhO | H | NH(CH$_2$)$_2$O(CH$_2$)$_2$O(CH$_2$)$_2$NH | 2 | 575 |
| 248 | 56 | H | 2-furyl-CONH | H | PhO | H | NH(CH$_2$)$_2$O(CH$_2$)$_2$O(CH$_2$)$_2$NH | 2 | 585 |
| 249 | 72 | H | 4-Me—PhCONH | H | PhO | H | NH(CH$_2$)$_2$O(CH$_2$)$_2$O(CH$_2$)$_2$NH | 2 | 609 |
| 250 | 78 | H | 4-Me—PhSO$_2$NH | H | PhO | H | NH(CH$_2$)$_2$O(CH$_2$)$_2$O(CH$_2$)$_2$NH | 2 | 645 |

TABLE 12

[Structure: dicinnamyl-N with ester and amide substituents, bracketed ×2]

| cpd | EPO/EBP-Ig % inh @ 50 μM | R$^a$ | R$^2$ | R$^4$ | Z | r | MS, [MH$_2$/2]+ |
| --- | --- | --- | --- | --- | --- | --- | --- |
| 251 | 49 | H | H | H | NH(CH$_2$)$_2$O(CH$_2$)$_2$O(CH$_2$)$_2$NH | 2 | 436 |
| 252 | −4 | t-Bu | 4-t-Bu—PhO | 4-t-Bu—PhO | NH(CH$_2$)$_3$O(CH$_2$)$_4$O(CH$_2$)$_3$NH | 1 | 803 |
| 253 | −5 | t-Bu | 4-t-Bu—PhO | 4-t-Bu—PhO | NH(CH$_2$)$_3$O(CH$_2$CH$_2$O)$_2$(CH$_2$)$_3$NH | 1 | 811 |
| 254 | −9 | t-Bu | 4-t-Bu—PhO | 4-t-Bu—PhO | NH(CH$_2$)$_{10}$NH | 1 | 787 |
| 255 | 0 | t-Bu | 4-t-Bu—PhO | 4-t-Bu—PhO | NH(CH$_2$)$_{12}$NH | 1 | 801 |
| 256 | 10 | t-Bu | 4-t-Bu—PhO | 4-t-Bu—PhO | NH(CH$_2$)$_2$O(CH$_2$)$_2$O(CH$_2$)$_2$NH | 1 | 789 |

TABLE 13

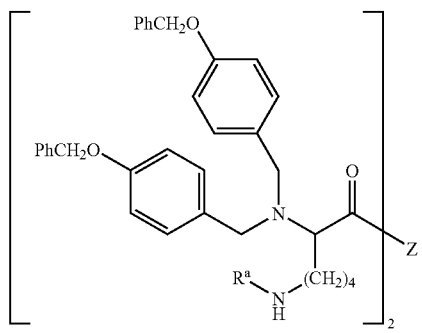

| cpd | EPO/EBP-Ig % inh @ 50 μM | R$^a$ | Z | MS, [MH$_2$/2]+ |
|---|---|---|---|---|
| 257 | −26 | Boc | NH(CH$_2$)$_3$O(CH$_2$CH$_2$O)$_2$(CH$_2$)$_3$NH | 731 |
| 258 | −24 | Boc | NH(CH$_2$)$_3$O(CH$_2$)$_4$O(CH$_2$)$_3$NH | 723 |
| 259 | −13 | Boc | NH(CH$_2$)$_{12}$NH | 721 |
| 260 | −12 | Boc | NH(CH$_2$)$_2$O(CH$_2$)$_2$O(CH$_2$)$_2$NH | 695 |
| 261 | 51 | H | NH(CH$_2$)$_2$O(CH$_2$)$_2$O(CH$_2$)$_2$NH | 595 |
| 262 | 93 | HO$_2$CCH$_2$CH$_2$CO | NH(CH$_2$)$_2$O(CH$_2$)$_2$O(CH$_2$)$_2$NH | 695 |
| 263 | 88 | HO$_2$C(CH$_2$)$_3$CO | NH(CH$_2$)$_2$O(CH$_2$)$_2$O(CH$_2$)$_2$NH | 709 |
| 264 | 89 | HO$_2$CCH$_2$CMe$_2$CH$_2$CO | NH(CH$_2$)$_2$O(CH$_2$)$_2$O(CH$_2$)$_2$NH | 737 |
| 265 | 65 | HO$_2$CCH$_2$CH$_2$CO | NH(CH$_2$)$_3$O(CH$_2$)$_4$O(CH$_2$)$_3$NH | 723 |
| 266 | 82 | HO$_2$C(CH$_2$)$_3$CO | NH(CH$_2$)$_3$O(CH$_2$)$_4$O(CH$_2$)$_3$NH | 737 |
| 267 | 83 | HO$_2$CCH$_2$CMe$_2$CH$_2$CO | NH(CH$_2$)$_3$O(CH$_2$)$_4$O(CH$_2$)$_3$NH | 765 |
| 268 | 40 | HO$_2$CCH$_2$CMe2CH$_2$CO | NH(CH$_2$)$_{12}$NH | 764 |
| 269 | 55 | HO$_2$CCH$_2$CH$_2$CH$_2$CO | NH(CH$_2$)$_{12}$NH | 735 |
| 270 | 56 | HO$_2$CCH$_2$CH$_2$CO | NH(CH$_2$)$_{12}$NH | 721 |
| 271 | 77 | HO$_2$CCH$_2$CH$_2$CO | NH(CH$_2$)$_3$O(CH$_2$CH$_2$O)$_2$(CH$_2$)$_3$NH | 731 |
| 272 | 78 | HO$_2$CCH$_2$CH$_2$CH$_2$CO | NH(CH$_2$)$_3$O(CH$_2$CH$_2$O)$_2$(CH$_2$)$_3$NH | 745 |

TABLE 14

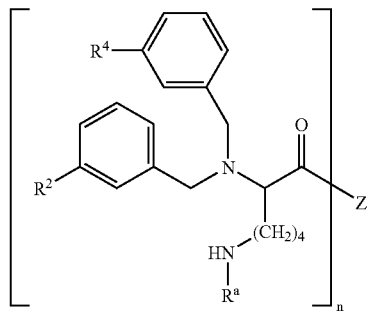

| cpd | EPO/EBP-Ig % inh @ 50 μM | R$^a$ | R$^2$ | R$^4$ | Z | n | MS, [MH$_2$/2]+ |
|---|---|---|---|---|---|---|---|
| 273 | nd | HO$_2$CCH$_2$CH$_2$CO | 4-Me—PhO | 4-Me—PhO | NH(CH$_2$)$_2$O(CH$_2$)$_2$O(CH$_2$)$_2$NH | 2 | 695 |
| 274 | nd | HO$_2$CCH$_2$CH$_2$CO | PhO | PhO | NH(CH$_2$)$_2$O(CH$_2$)$_2$O(CH$_2$)$_2$NH | 2 | 667 |
| 275 | nd | HO$_2$CCH$_2$CH$_2$CO | 4-Me—PhO | 4-Me—PhO | NH(CH$_2$)$_2$O(CH$_2$)$_2$O(CH$_2$)$_2$NH | 2 | 727 |
| 276 | nd | HO$_2$CCH$_2$CH$_2$CO | 4-t-Bu—PhO | 4-t-Bu—PhO | NH(CH$_2$)$_2$O(CH$_2$)$_2$O(CH$_2$)$_2$NH | 2 | 780 |
| 277 | nd | H | PhO | PhO | (NHCH$_2$CH$_2$)$_3$N | 3 | 813 |
| 278 | nd | H | 4-Me—PhO | 4-Me—PhO | (NHCH$_2$CH$_2$)$_3$N | 3 | 855 |
| 279 | nd | H | 4-Me—PhO | 4-Me—PhO | (NHCH$_2$CH$_2$)$_3$N | 3 | 903 |
| 280 | nd | HO$_2$CCH$_2$CH$_2$CO | 4-Me—PhO | 4-Me—PhO | (NHCH$_2$CH$_2$)$_3$N | 3 | 1053 |
| 281 | nd | HO$_2$CCH$_2$CH$_2$CO | 4-Me—PhO | 4-Me—PhO | (NHCH$_2$CH$_2$)$_3$N | 3 | 1005 |
| 282 | nd | HO$_2$CCH$_2$CH$_2$CO | PhO | PhO | (NHCH$_2$CH$_2$)$_3$N | 3 | 963 |
| 283 | nd | Boc | PhO | PhO | NH(CH$_2$)$_3$NMe(CH$_2$)$_3$NH | 2 | 666 |
| 284 | nd | Boc | 4-Me—PhO | 4-Me—PhO | NH(CH$_2$)$_3$NMe(CH$_2$)$_3$NH | 2 | 694 |

TABLE 15

| cpd | EPO/EBP-Ig % inh @ 50 μM | R¹ | R² | R³ | MS, MH+ |
|---|---|---|---|---|---|
| 285 | −28 | Me | H | H | 473 |
| 286 | 46 | H | BnO | H | 565 |
| 287 | 36 | H | 4-Me—PhO | H | 565 |
| 288 | 27 | H | 4-tBu—PhO | H | 607 |
| 289 | 20 | H | H | PhO | 551 |

TABLE 16A

| cpd | EPO/EBP-Ig % inh @ 50 μM | R¹ | R² | R³ | R⁴ |
|---|---|---|---|---|---|
| 290 | 0 | Me | PhO | H | t-Bu |
| 291 | 17 | Me | H | Ph | t-Bu |
| 292 | 11 | Me | 3-CF3—C6H4O | H | t-Bu |
| 293 | 14 | Me | 3,4-Cl2—C6H3O | H | t-Bu |
| 294 | 9 | Me | 4-t-Bu—C6H4O | H | t-Bu |
| 295 | 10 | Me | H | Ph | H |
| 296 | 0 | Me | 3,4-Cl2—C6H3O | H | H |
| 297 | 0 | Me | 3-CF3—C6H4O | H | H |
| 298 | 1 | Me | 4-t-Bu—C6H4O | H | H |
| 299 | nd | Me | PhO | H | H |
| 300 | 57 | H | PhO | H | H |
| 301 | 25 | H | H | Ph | t-Bu |
| 302 | 30 | H | 3,4-Cl2—C6H3O | H | t-Bu |
| 303 | 21 | H | 3-CF3—C6H4O | H | t-Bu |
| 304 | 19 | H | 4-t-Bu—C6H4O | H | t-Bu |
| 305 | 48 | H | H | Ph | H |
| 306 | 21 | Me | H | H | t-Bu |
| 307 | 25 | H | 3,4-Cl2—C6H3O | H | H |
| 308 | 25 | H | 3-CF3—C6H4O | H | H |
| 309 | 13 | H | 4-t-Bu—C6H4O | H | H |
| 310 | 34 | Me | H | H | H |

TABLE 16B

| cpd | MPLC solvent | appearance | empirical formula | MS, MH+ |
|---|---|---|---|---|
| 290 | 10-30% EtOAc/hex | pale yellow oil | C38H41NO5 | 592 |
| 291 | 1:5 EtOAc/hex | yellow oil | C38H41NO3 | 560 |
| 292 | 1:5 EtOAc/hex | yellow oil | C40H39F6NO5 | 728 |
| 293 | 1:5 EtOAc/hex | yellow oil | C38H37C14NO5 | 728 |
| 294 | 1:5 EtOAc/hex | yellow oil | C46H57NO5 | 704 |
| 295 | | off-white solid | C34H33NO3/1 C2H4O2 | 504 |
| 296 | | amber solid | C34H29C14NO5/1 C2H4O2 | 672 |
| 297 | | amber oil | C36H31F6NO5/1 C2H4O2 | 672 |
| 298 | | off-white solid | C42H49NO5/1 C2H4O2 | 648 |
| 299 | 30% EtOAc/hex | colorless oil | C34H33NO5 | 536 |
| 300 | | sticky yellow solid | C33H31NO5/1 C2H4O2 | 522 |
| 301 | | yellow solid | C37H39NO3 | 546 |
| 302 | | amber oil | C37H35C14NO5 | 714 |
| 303 | | amber oil | C39H37F6NO5 | 714 |
| 304 | | amber oil | C45H55NO5 | 690 |
| 305 | | amber solid | C33H31NO2/1 C2HF3O2 | 490 |
| 306 | | light-yellow oil | C26H33NO3/0.25 H2O | 408 |
| 307 | | amber solid | C33H27C14NO5/1 C2HF3O2 | 658 |
| 308 | | amber oil | C35H29F6NO5/1 C2HF3O2 | 658 |
| 309 | | off-white solid | C41H47NO5/1 C2HF3O2 | 634 |
| 310 | | light yellow oil | C22H25NO3/1 C2H4O2 | 352 |

TABLE 17A

| cpd | EPO/EBP-Ig % inh @ 50 μM | R¹ | R² | R³ |
|---|---|---|---|---|
| 311 | 5.3 | t-Bu | PhO | H |
| 312 | 45 | H | PhO | H |

TABLE 17B

| cpd | MPLC solvent | appearance | empirical formula | MS, MH+ |
|---|---|---|---|---|
| 311 | 10% EtOAc/hex | pale yellow oil | C36H37NO4 | 548 |
| 312 | | sticky brown solid | C32H29NO4/1 C2HF3O2 | 492 |

TABLE 18A

| cpd | EPO/EBP-Ig % inh @ 50 μM | R¹ | R² | R³ | R⁴ |
|---|---|---|---|---|---|
| 313 | 28 | H | H | CF3 | (CH2)4NH(2-Cl—Cbz) |
| 314 | 12 | Me | H | CO2H | (CH2)4NH2 |
| 315 | nd | Me | H | NO2 | (CH2)4NHBoc |
| 316 | 20 | Me | OPh | H | (CH2)4NHBoc |
| 317 | 13 | Me | 4-t-Bu—C6H4O | H | (CH2)4NHBoc |
| 318 | 14 | Me | H | H | (CH2)4NHCbz |
| 319 | nd | Me | H | H | (CH2)4NHCbz |
| 320 | 17 | Me | H | OMe | (CH2)4NHCbz |
| 321 | 42 | Me | CO2Me | H | (CH2)4NHCbz |
| 322 | nd | Me | H | 2,3-benzo | (CH2)4NHCbz |
| 323 | 6 | Me | H | CO2H | (CH2)4NHCbz |
| 324 | nd | Me | H | CO2Me | nd |

TABLE 18B

| cpd | MPLC solvent | appearance | empirical formula | MS, MH+ |
|---|---|---|---|---|
| 313 | | yellow oil | C25H28ClF3N2O4\1 C2HF3O2 | 499 |
| 314 | | yellow oil | C17H24N2O4 | 321 |
| 315 | 30% EtOAc/hex | dark yellow gum | C21H31N3O6 | 422 |
| 316 | 20-50% EtOAc/hex | pale yellow oil | C27H36N2O5 | 469 |
| 317 | | pale yellow oil | C31H44N2O5 | 525 |
| 318 | | gum | C24H30N2O4 | 411 |
| 319 | | pale yellow oil | C24H30N2O4 | 411 |
| 320 | 2% MeOH/CH2Cl2 | yellow oil | C25H32N2O5 | 441 |
| 321 | | yellow oil | C26H32N2O6\1 C2H4O2 | 469 |
| 322 | 25-50% EtOAc/hex | clear residue | C28H32N2O4 | 461 |
| 323 | | yellow oil | C25H30N2O6 | 455 |
| 324 | | yellow oil | C26H32N2O6 | 469 |

TABLE 19A

| cpd | EPO/EBP-Ig % inh @ 50 μM | R¹ | R² | R³ | R⁴ |
|---|---|---|---|---|---|
| 325 | 6 | Me | OPh | H | CH2CH2CO2H |
| 326 | 0 | H | OPh | H | CH2CH2CO2H |
| 327 | 11 | Me | H | Ph | CH2CH2CO2H |
| 328 | 33 | Me | 3,4-Cl2—C6H3O | H | CH2CH2CO2H |
| 329 | 13 | H | H | Ph | CH2CH2CO2H |
| 330 | 12 | H | 3-CF3—C6H4O | H | CH2CH2CO2H |
| 331 | 18 | H | 4-t-Bu—C6H4O | H | CH2CH2CO2H |
| 332 | 17 | H | 3,4-Cl2—C6H3O | H | CH2CH2CO2H |
| 333 | 16 | Me | 3,4-benzo | | CH2CH2CO2-t-Bu |
| 334 | 6 | Me | OPh | H | CH2CH2CO2-t-Bu |
| 335 | 25 | Me | H | Ph | CH2CH2CO2-t-Bu |
| 336 | 32 | Me | 3,4-Cl2—C6H3O | H | CH2CH2CO2-t-Bu |
| 337 | 0 | H | OPh | H | CH2CH2CO2-t-Bu |
| 338 | 23 | t-Bu | 3-CF3—C6H4O | H | CH2CH2CO2-t-Bu |
| 339 | 10 | t-Bu | 4-t-Bu—C6H4O | H | CH2CH2CO2-t-Bu |
| 340 | 14 | H | H | Ph | CH2CH2CO2-t-Bu |
| 341 | 19 | H | 3,4-Cl2—C6H3O | H | CH2CH2CO2-t-Bu |

TABLE 19B

| cpd | MPLC solvent | appearance | empirical formula | MS, MH+ |
|---|---|---|---|---|
| 325 |  | off-white solid | C21H23NO5\1C2F3HO2 | 370 |
| 326 |  | fluffy white solid | C20H21NO5\1C2HF3O2 | 356 |
| 327 |  | off-white solid | C21H23NO4\1C2F3HO2 | 354 |
| 328 |  | amber oil | C21H21Cl2NO5\1C2F3HO2 | 438 |
| 329 |  | amber solid | C20H21NO4\1C2HF3O2 | 340 |
| 330 |  | amber oil | C21H20F3NO5\1C2HF3O2 | 424 |
| 331 |  | amber oil | C24H29NO5\1C2HF3O2 | 412 |
| 332 |  | amber oil | C20H19CL2NO5\1C2HF3O2 | 424 |
| 333 | 10-25% EtOAc/hex | yellow oil | C23H29NO4 | 384 |
| 334 | 10-30% EtOAc/hex | pale yellow oil | C25H31NO5 | 426 |
| 335 | 1:5 EtOAc/hex | yellow oil | C25H31NO4 | 410 |
| 336 | 1:5 EtOAc/hex | yellow oil | C25H29Cl2NO5 | 494 |
| 337 |  | white powder | C24H29NO5\0.4H2O | 412 |
| 338 | 1:5 EtOAc/hex | yellow oil | C29H36F3NO5 | 536 |
| 339 | 1:5 EtOAc/hex | yellow oil | C32H45NO5 | 524 |
| 340 |  | yellow solid | C24H29NO4 | 396 |
| 341 |  | white solid | C24H27Cl2NO5 | 480 |

TABLE 20A

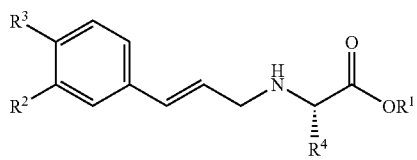 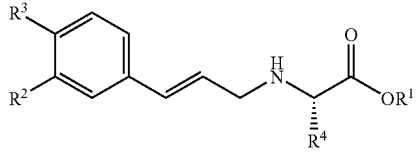

| cpd | EPO/EBP-Ig % inh @ 50 µM | R1 | R2 | R3 | R4 |
|---|---|---|---|---|---|
| 342 | 0 | Me | H | Ph | CH2OH |
| 343 | 37 | Me | 4-t-Bu—C6H4O | H | CH2OH |
| 344 | 4 | Me | 3-CF3—C6H4O | H | CH2OH |
| 345 | 40 | Me | 3,4-Cl2—C6H3O | H | CH2OH |
| 346 | 28 | Me | OPh | H | CH2OH |
| 347 | 23 | H | OPh | H | CH2OH |
| 348 | 21 | H | H | Ph | CH2OH |
| 349 | 23 | H | 3,4-Cl2—C6H3O | H | CH2OH |
| 350 | 23 | H | 3-CF3—C6H4O | H | CH2OH |
| 351 | 29 | H | 4-t-Bu—C6H4O | H | CH2OH |
| 352 | 8 | Me | OPh | H | CH2O-t-Bu |
| 353 | 24 | Me | H | Ph | CH2O-t-Bu |
| 354 | 31 | Me | 3,4-Cl2—C6H3O | H | CH2O-t-Bu |
| 355 | 22 | Me | 3-CF3—C6H4O | H | CH2O-t-Bu |
| 356 | 23 | Me | 4-t-Bu—C6H4O | H | CH2O-t-Bu |
| 357 | 12 | H | 3-CF3—C6H4O | H | CH2O-t-Bu |

TABLE 20B

| cpd | MPLC solvent | appearance | empirical formula | MS, MH+ |
|---|---|---|---|---|
| 342 |  | off-white solid | C19H21NO3\1C2F3HO2 | 312 |
| 343 |  | amber oil | C23H29NO4\1C2F3HO2 | 384 |
| 344 |  | amber oil | C20H20F3NO4\1C2F3HO2 | 396 |
| 345 |  | amber oil | C19H19Cl2NO4\1C2F3HO2 | 396 |

TABLE 20B-continued

| cpd | MPLC solvent | appearance | empirical formula | MS, MH+ |
|---|---|---|---|---|
| 346 | EtOAc | pale yellow oil | C19H21NO4 | 328 |
| 347 | | amber oil | C18H19NO4\1 C2HF3O2 | 314 |
| 348 | | yellow solid | C18H19NO3\1 C2HF3O2 | 298 |
| 349 | | amber oil | C18H17Cl2NO4\1 C2HF3O2 | 382 |
| 350 | | amber oil | C19H18F3NO4\1 C2HF3O2 | 382 |
| 351 | | amber oil | C22H27NO4\1 C2HF3O2 | 370 |
| 352 | 10-30% EtOAc/hex | pale yellow oil | C23H29NO4 | 384 |
| 353 | 20% EtOAc/hex | off-white solid | C23H29NO3 | 368 |
| 354 | 20% EtOAc/hex | yellow oil | C23H27Cl2NO4 | 452 |
| 355 | 20% EtOAc/hex | yellow oil | C24H28F3NO4 | 452 |
| 356 | 20% EtOAc/hex | yellow oil | C27H37NO4 | 440 |
| 357 | | white solid | C23H26F3NO4 | 438 |

TABLE 21A

| cpd | EPO/EBP-Ig % inh @ 50 μM | $R^1$ | $R^2$ | $R^3$ | $R^4$ |
|---|---|---|---|---|---|
| 358 | 0 | H | H | CF3 | (s)-CH(OH)CH3 |
| 359 | 25 | Me | CO2Me | H | (s)-CH(OMe)CH3 |
| 360 | 18 | Me | H | H | Bn |
| 361 | 24 | Me | CO2Me | H | Bn |
| 362 | 0 | H | H | CF3 | CH2(4-HOC6H4) |
| 363 | 33 | Me | CO2Me | H | CH2(4-MeOC6H4) |
| 364 | 16 | Me | H | H | CH2(indol-3-yl) |
| 365 | 0 | H | H | CF3 | CH2CH2SMe |
| 366 | 38 | Me | CO2Me | H | CH2CO2Me |
| 367 | 0 | H | H | CF3 | CH2CONH2 |
| 368 | 40 | Me | CO2Me | H | CH2SBn |
| 369 | 12 | H | H | CF3 | i-Bu |
| 370 | 0 | H | H | CF3 | i-Pr |
| 371 | 16 | Me | CO2Me | H | i-Pr |
| 372 | 0 | Me | H | H | Me |

TABLE 21B

| cpd | MPLC solvent | appearance | empirical formula | MS, MH+ |
|---|---|---|---|---|
| 358 | | amber oil | C14H16F3NO3\1 C2HF3O2 | 304 |
| 359 | | amber oil | C17H23NO5\1 C2H4O2 | 322 |
| 360 | 20% EtOAc/hex | light-yellow oil | C19H21NO2 | 296 |
| 361 | | amber oil | C22H25NO5\1 C2H4O2 | 354 |
| 362 | | amber oil | C19H18F3NO3\1 C2HF3O2 | 366 |
| 363 | | amber oil | C22H25NO5\1 C2H4O2 | 384 |
| 364 | 1:2 EtOAc/hex | tan solid | C21H22N2O2 | 335 |
| 365 | | amber oil | C15H18F3NO2S\1 C2HF3O2 | 334 |
| 366 | | amber oil | C17H21NO6\1 C2H4O2 | 336 |
| 367 | | amber oil | C14H15F3N2O3\1 C2HF3O2 | 317 |
| 368 | | amber oil | C22H25NO4S\1 C2H4O2 | 400 |
| 369 | | amber oil | C17H22F3NO2\1 C2HF3O2 | 316 |
| 370 | | amber oil | C15H18F3NO2\1 C2HF3O2 | 302 |
| 371 | | amber oil | C17H23NO4\1 C2H4O2 | 306 |
| 372 | 20% EtOAc/hex | yellow oil | C13H17NO2\0.10 C4H8O2 | 220 |

What is claimed is:

1. A pharmaceutical composition comprising a compound of the formula:

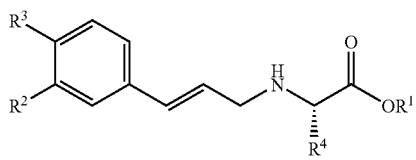

wherein:

$R^1$ is H or $C_{1-5}$alkyl;

$R^2$ is H, phenoxy, benzyl, substituted phenoxy (where the substituents are selected from $C_{1-5}$alkyl, $C_{1-5}$alkoxy, hydroxy, halo, trifluoromethyl, nitro, cyano, and amino), or $CO_2Me$;

$R^3$ is H, phenyl, triflouromethyl; and $R^4$ is the side chain of a natural or unnatural α-amino acid, where if said side chain contains a protectable group, that group may be protected with a member of the group consisting of succinyl, glutaryl, 3,3-dimethylglutaryl, $C_{1-5}$alkyl, $C_{1-5}$alkoxycarbonyl, acetyl, N-(9-flourenylmethoxycarbonyl), trifluoroacetyl, omega-carboxy$C_{1-5}$alkylcarbonyl, t-butoxycarbonyl, benzyl, benzyloxycarbonyl, 2-chlorobenzyloxycarbonyl, phenylsulfonyl, ureido, t-butyl, cinnamoyl, trityl, 4-methyltrityl, 1-(4,4-dimethyl-2,6-dioxocyclohexylidene) ethyl, tosyl, 4-methoxy-2,3,6-trimethylbenzenesulfonyl, phenylureido, and substituted phenylureido(where the phenyl substituents are phenoxy, halo, $C_{1-5}$alkoxycarbonyl).

2. A pharmaceutical composition comprising an active drug component and the compound of claim 1.

3. The composition of claim 2 wherein said active drug component is combined with an oral, non-toxic pharmaceutically acceptable inert carrier.

4. The composition of claim 3 wherein said carrier is ethanol, glycerol, or water.

5. The composition of claim 2 further comprising binders, lubricants, disintegrating agents, or coloring agents.

6. The composition of claim 5 wherein said binders are selected from the group consisting of starch, gelatin, natural sugars, corn sweeteners, natural and synthetic gums carboxymethylcellulose, polyethylene glycol, and waxes.

7. The composition of claim 5 wherein said lubricants are selected from the group consisting of sodium oleate, sodium stearate, magnesium stearate, sodium benzoate, sodium acetate, and sodium chloride.

8. The composition of claim 5 wherein said disintegrating agents are selected from the group consisting of starch, methyl cellulose, agar, bentonite, and xanthan gum.

9. The composition of claim 2 contained in a topical administration.

10. The composition of claim 9 wherein said active drug component can be admixed with carrier materials selected from the group consisting of alcohols, aloe vera gel, allontoin, glycerine, vitamin A and E oils, mineral oil, PPG2 myristyl propionate.

11. An oral composition comprising an EPO receptor modulating compound comprising the compound of claim 1 having an active drug component being combined with an oral, non-toxic pharmaceutically acceptable inert carrier.

12. The composition of claim 11 wherein said carrier is ethanol, glycerol, or water.

13. The composition of claim 11 further comprising binders, lubricants, disintegrating agents, or coloring agents.

14. The composition of claim 13 wherein said binders are selected from the group consisting of starch, gelatin, natural sugars, corn sweeteners, natural and synthetic gums carboxymethylcellulose, polyethylene glycol, and waxes.

15. The composition of claim 13 wherein said lubricants are selected from the group consisting of sodium oleate, sodium stearate, magnesium stearate, sodium benzoate, sodium acetate, and sodium chloride.

16. The composition of claim 13 wherein said disintegrating agents are selected from the group consisting of starch, methyl cellulose, agar, bentonite, and xanthan gum.

* * * * *